US010687690B2

(12) United States Patent
Kesten et al.

(10) Patent No.: US 10,687,690 B2
(45) Date of Patent: Jun. 23, 2020

(54) GUIDE CATHETER WITH IMAGE CAPTURE AND LIGHT EMISSION FEATURES

(71) Applicant: Acclarent, Inc., Irvine, CA (US)

(72) Inventors: Randy J. Kesten, Mountain View, CA (US); Ketan P. Muni, San Jose, CA (US); James Patrick Garvey, II, Mountain View, CA (US); Hung V. Ha, San Jose, CA (US); Andy Nguyen, San Jose, CA (US)

(73) Assignee: Acclarent, Inc., Irvine, CA (US)

( * ) Notice: Subject to any disclaimer, the term of this patent is extended or adjusted under 35 U.S.C. 154(b) by 0 days.

(21) Appl. No.: 15/928,171

(22) Filed: Mar. 22, 2018

(65) Prior Publication Data

US 2018/0279855 A1    Oct. 4, 2018

Related U.S. Application Data

(62) Division of application No. 14/826,400, filed on Aug. 14, 2015, now Pat. No. 9,955,852.
(Continued)

(51) Int. Cl.
*A61B 1/00* (2006.01)
*A61B 1/012* (2006.01)
(Continued)

(52) U.S. Cl.
CPC ...... *A61B 1/00082* (2013.01); *A61B 1/00087* (2013.01); *A61B 1/00135* (2013.01);
(Continued)

(58) Field of Classification Search
None
See application file for complete search history.

(56) References Cited

U.S. PATENT DOCUMENTS 4,960,410 A * 10/1990 Pinchuk ............ A61M 25/0054
604/103.1
5,411,514 A * 5/1995 Fucci ............... A61B 17/32002
606/180
(Continued)

FOREIGN PATENT DOCUMENTS

EP          2692386 A1    2/2014
JP       2008-536552 A   12/2005
(Continued)

OTHER PUBLICATIONS

St. Croix, B. et al., "Genes Expressed in Human Tumor Endothelium," Science, Aug. 18, 2000, 289(5482): 1197-1201, 6 pages.
(Continued)

*Primary Examiner* — Timothy J Neal
(74) *Attorney, Agent, or Firm* — Frost Brown Todd LLC

(57) ABSTRACT

A dilation catheter system comprises a guide member, a dilation catheter, and an image sensor. The guide member includes a shaft comprising a distal end and a proximal end. The shaft further defines a longitudinal axis. The dilation catheter is movable relative to the guide catheter member and comprises an expandable dilator. The expandable dilator is sized to fit within one or both of a Eustachian tube or a passageway associated with a paranasal sinus. The image sensor is configured to provide visualization within anatomy of a patient. The image sensor is integral with the guide member.

20 Claims, 21 Drawing Sheets

Related U.S. Application Data

(60) Provisional application No. 62/140,104, filed on Mar. 30, 2015.

(51) Int. Cl.

| | | |
|---|---|---|
| *A61B 1/018* | (2006.01) | |
| *A61B 1/233* | (2006.01) | |
| *A61B 17/24* | (2006.01) | |
| *A61M 29/02* | (2006.01) | |
| *A61B 17/34* | (2006.01) | |
| *A61M 25/00* | (2006.01) | |
| *A61M 25/06* | (2006.01) | |
| *A61F 11/00* | (2006.01) | |
| *A61B 1/05* | (2006.01) | |
| *A61B 1/06* | (2006.01) | |
| *A61B 1/227* | (2006.01) | |
| *A61B 17/29* | (2006.01) | |
| *A61M 25/01* | (2006.01) | |
| *A61M 25/10* | (2013.01) | |
| *A61B 17/00* | (2006.01) | |
| *A61B 90/00* | (2016.01) | |
| *A61B 90/30* | (2016.01) | |

(52) U.S. Cl.
CPC .............. *A61B 1/012* (2013.01); *A61B 1/018* (2013.01); *A61B 1/05* (2013.01); *A61B 1/0623* (2013.01); *A61B 1/0684* (2013.01); *A61B 1/227* (2013.01); *A61B 1/233* (2013.01); *A61B 17/24* (2013.01); *A61B 17/29* (2013.01); *A61B 17/3421* (2013.01); *A61F 11/002* (2013.01); *A61M 25/0041* (2013.01); *A61M 25/01* (2013.01); *A61M 25/0662* (2013.01); *A61M 25/10* (2013.01); *A61M 29/02* (2013.01); *A61B 90/361* (2016.02); *A61B 2017/00331* (2013.01); *A61B 2017/00787* (2013.01); *A61B 2017/345* (2013.01); *A61B 2090/306* (2016.02); *A61M 25/0054* (2013.01); *A61M 25/0068* (2013.01); *A61M 2025/0046* (2013.01); *A61M 2025/0681* (2013.01); *A61M 2029/025* (2013.01); *A61M 2205/32* (2013.01); *A61M 2210/0675* (2013.01); *A61M 2210/0681* (2013.01)

(56) References Cited

U.S. PATENT DOCUMENTS

| | | | | |
|---|---|---|---|---|
| 5,843,050 | A * | 12/1998 | Jones | A61M 25/0012 604/525 |
| 5,961,510 | A * | 10/1999 | Fugoso | A61M 25/0054 604/524 |
| 6,066,090 | A | 5/2000 | Yoon | |
| 6,716,813 | B2 | 4/2004 | Lim et al. | |
| 6,939,327 | B2 | 9/2005 | Hall et al. | |
| 8,317,689 | B1 * | 11/2012 | Remijan | A61B 1/00142 600/112 |
| 8,888,686 | B2 | 11/2014 | Drontle et al. | |
| 9,155,492 | B2 | 10/2015 | Jenkins et al. | |
| 9,289,582 | B2 | 3/2016 | Suehara | |
| 9,955,852 | B2 * | 5/2018 | Kesten | A61B 1/233 |
| 10,258,240 | B1 * | 4/2019 | Eberle | A61B 5/0084 |
| 2003/0125709 | A1 * | 7/2003 | Eidenschink | A61M 25/0662 604/524 |
| 2003/0212373 | A1 | 11/2003 | Hall et al. | |
| 2003/0225434 | A1 * | 12/2003 | Glantz | A61M 25/0009 606/194 |
| 2004/0199053 | A1 | 10/2004 | Boulais et al. | |
| 2005/0154262 | A1 | 7/2005 | Banik et al. | |
| 2006/0004323 | A1 | 1/2006 | Chang et al. | |
| 2006/0063973 | A1 * | 3/2006 | Makower | A61B 1/00135 600/114 |
| 2006/0149129 | A1 * | 7/2006 | Watts | A61B 1/00135 600/113 |
| 2007/0225750 | A1 | 9/2007 | Ren et al. | |
| 2008/0172033 | A1 | 7/2008 | Keith et al. | |
| 2010/0030031 | A1 | 2/2010 | Goldfarb et al. | |
| 2010/0274188 | A1 | 10/2010 | Chang et al. | |
| 2011/0004057 | A1 | 1/2011 | Goldfarb et al. | |
| 2012/0238805 | A1 | 9/2012 | Iwasaka et al. | |
| 2013/0041214 | A1 | 2/2013 | Maahs et al. | |
| 2013/0144122 | A1 * | 6/2013 | Adair | H04N 5/3765 600/110 |
| 2013/0274715 | A1 * | 10/2013 | Chan | A61M 25/10 604/514 |
| 2014/0088355 | A1 * | 3/2014 | Schaeffer | A61M 25/0136 600/109 |
| 2014/0261545 | A1 | 9/2014 | Jenkins et al. | |
| 2014/0261579 | A1 | 9/2014 | Jenkins et al. | |
| 2015/0031946 | A1 | 1/2015 | Saadat et al. | |
| 2015/0051449 | A1 | 2/2015 | Qiu | |
| 2015/0196738 | A1 | 7/2015 | Yamazaki et al. | |
| 2015/0374963 | A1 | 12/2015 | Chan et al. | |
| 2016/0287059 | A1 | 10/2016 | Ha et al. | |

FOREIGN PATENT DOCUMENTS

| | | |
|---|---|---|
| WO | WO 2013/122056 A1 | 8/2013 |
| WO | WO 2014/050620 A1 | 4/2014 |

OTHER PUBLICATIONS

Partial International Search Report dated Jun. 24, 2016 re Application No. PCT/US2016/024716.
International Search Report and Written Opinion dated Aug. 19, 2016 re Application No. PCT/US2016/024716.
International Search Report and Written Opinion dated Jun. 30, 2016 for Application No. PCT/US2016/024728, 11 pages.
Non-Final Office Action, dated Jul. 20, 2017, for U.S. Appl. No. 14/826,400, 15 pages.
Non-Final Office Action, dated Apr. 18, 2017, for U.S. Appl. No. 14/826,412, 12 pages.
Final Office Action, dated Jul. 27, 2017, for U.S. Appl. No. 14/826,412, 24 pages, 24 pages.
U.S. Appl. No. 62/139,933, filed Mar. 30, 2015.
U.S. Appl. No. 62/140,104, filed Mar. 30, 2015.
Partial European Search Report dated Nov. 7, 2019 for Application No. 19186576.5, 11 pages.
Japanese Notification of Reasons for Refusal dated Mar. 10, 2020 for Application No. 2017-551308, 5 pages.
Chinese Office Action, The Second Office Action, and Supplementary Search Report, dated Mar. 30, 2020 for Application No. CN 201680031824.2, 8 pgs.

\* cited by examiner

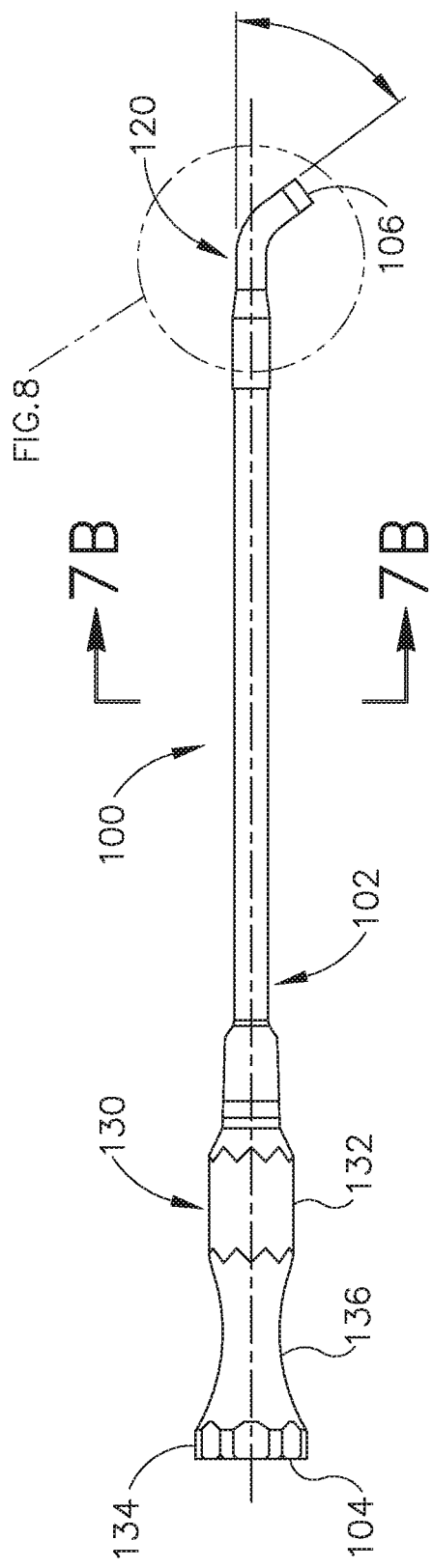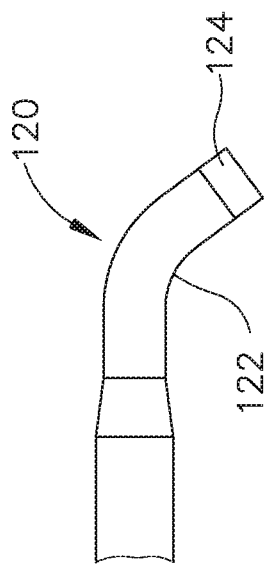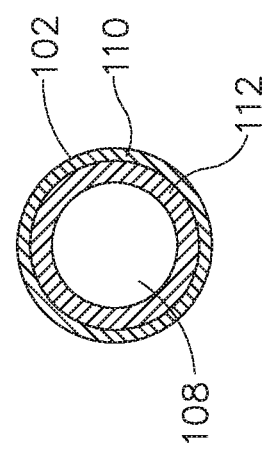
Fig.7A
Fig.7B
Fig.8

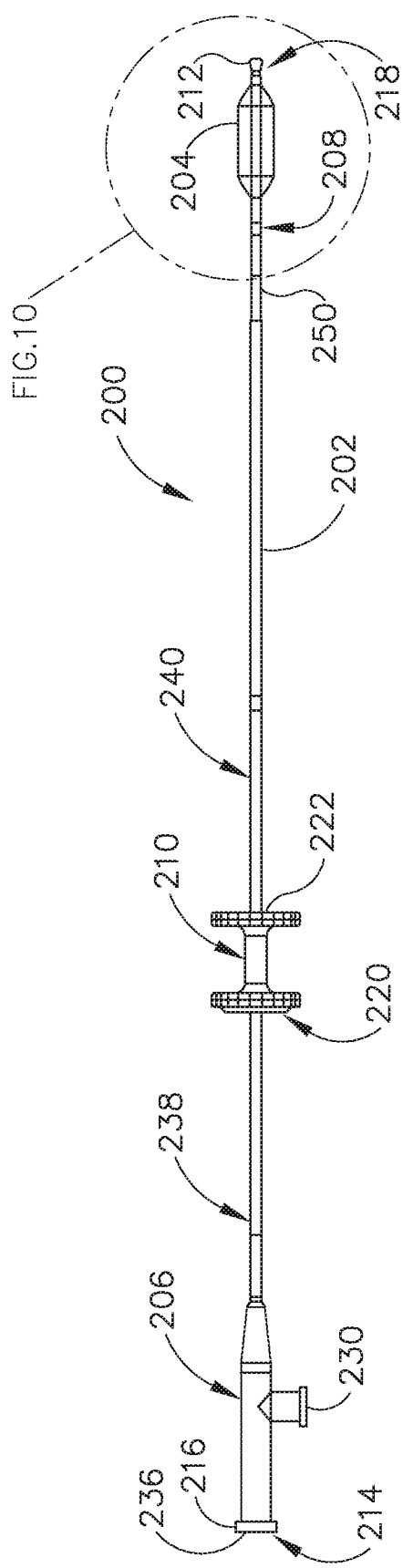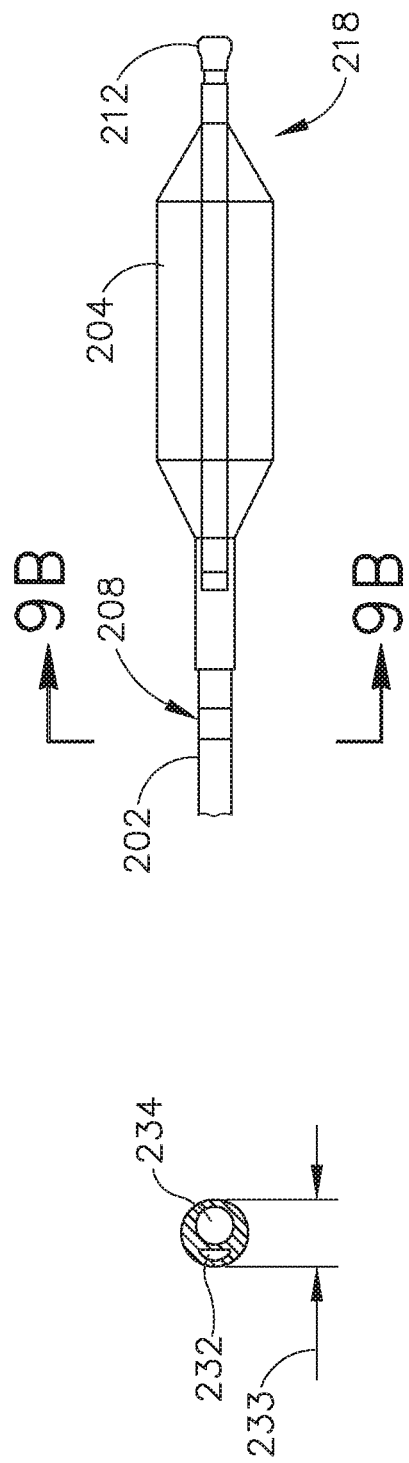
Fig. 9A
Fig. 9B
Fig. 10

GUIDE CATHETER WITH IMAGE CAPTURE AND LIGHT EMISSION FEATURES

PRIORITY

This application is a divisional of U.S. patent application Ser. No. 14/826,400 filed Aug. 14, 2015, now U.S. Pat. No. 9,955,852, issued on May 1, 2018, which claims priority to U.S. Provisional Patent App. No. 62/140,104, entitled "Guide Catheter with Image Capture and Light Emission Features," filed. Mar. 30, 2015, the disclosure of which is incorporated by reference herein.

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guide catheter to position an dilation catheter within the anatomical passageway, then inflating a balloon disposed on the dilation catheter with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, now abandoned, the disclosure of which is incorporated by reference herein. An example of such a system is the Relieva® Spin Balloon Sinuplasty™ System by Acclarent, Inc. of Menlo Park, Calif.

Alternatively such dilation catheters may also be employed using a similar method for the dilation of a Eustachian tube located adjacent to the paranasal sinus of a patent. A system that may be used to perform such procedures may be provided in accordance with the teachings of U.S. patent application Ser. No. 14/317,269, entitled "Vent Cap for a Eustachian Tube Dilation System," filed Jun. 29, 2014, issued as U.S. Pat. No. 10,350,396 on Jul. 16, 2019, the disclosure of which is incorporated by reference herein.

A variable direction view endoscope may be used with such a system to provide visualization within the anatomical passageway (e.g., the ear, nose, throat, paranasal sinuses, etc.) to position the balloon at desired locations. A variable direction view endoscope may enable viewing along a variety of transverse viewing angles without having to flex the shaft of the endoscope within the anatomical passageway. Such an endoscope that may be provided in accordance with the teachings of U.S. Pub. No. 2010/0030031, entitled "Swing Prism Endoscope," published Feb. 4, 2010, now abandoned, the disclosure of which is incorporated by reference herein. An example of such an endoscope is the Acclarent Cyclops™ Multi-Angle Endoscope by Acclarent, Inc. of Menlo Park, Calif.

While a variable direction view endoscope may be used to provide visualization within the anatomical passageway, it may also be desirable to provide additional visual confirmation of the proper positioning of the balloon before inflating the balloon. Alternatively, it may be desirable to eliminate the endoscope altogether when patient anatomy proves too small and/or tortuous for full visualization using such an endoscope. In either case, this may be accomplished using imaging sensors positioned on either the guide catheter or the balloon catheter, or both the guide catheter and the dilation catheter. Such imaging sensors may be positioned within or near to the target area and be used to visualize the target area.

It may be desirable to provide easily controlled inflation/deflation of a balloon in dilation procedures, including procedures that will be performed only by a single operator. While several systems and methods have been made and used to inflate an inflatable member such as a dilation balloon, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 7A depicts a side elevational view of an exemplary guide catheter;

FIG. 7B depicts a cross-sectional view of a shaft of the guide catheter of FIG. 7A, the cross-section taken along line 7B-7B of FIG. 7A;

FIG. 8 depicts a detailed side view of the guide catheter of FIG. 7A;

FIG. 9A depicts a side elevational view of an exemplary dilation catheter for use with the guide catheter of FIG. 7A;

FIG. 9B depicts a cross-sectional view of a shaft of the dilation catheter of FIG. 9A, the cross-section taken along line 9B-9B of FIG. 10;

FIG. 10 depicts a detailed side view of the dilation catheter of FIG. 9A;

Figure 1:
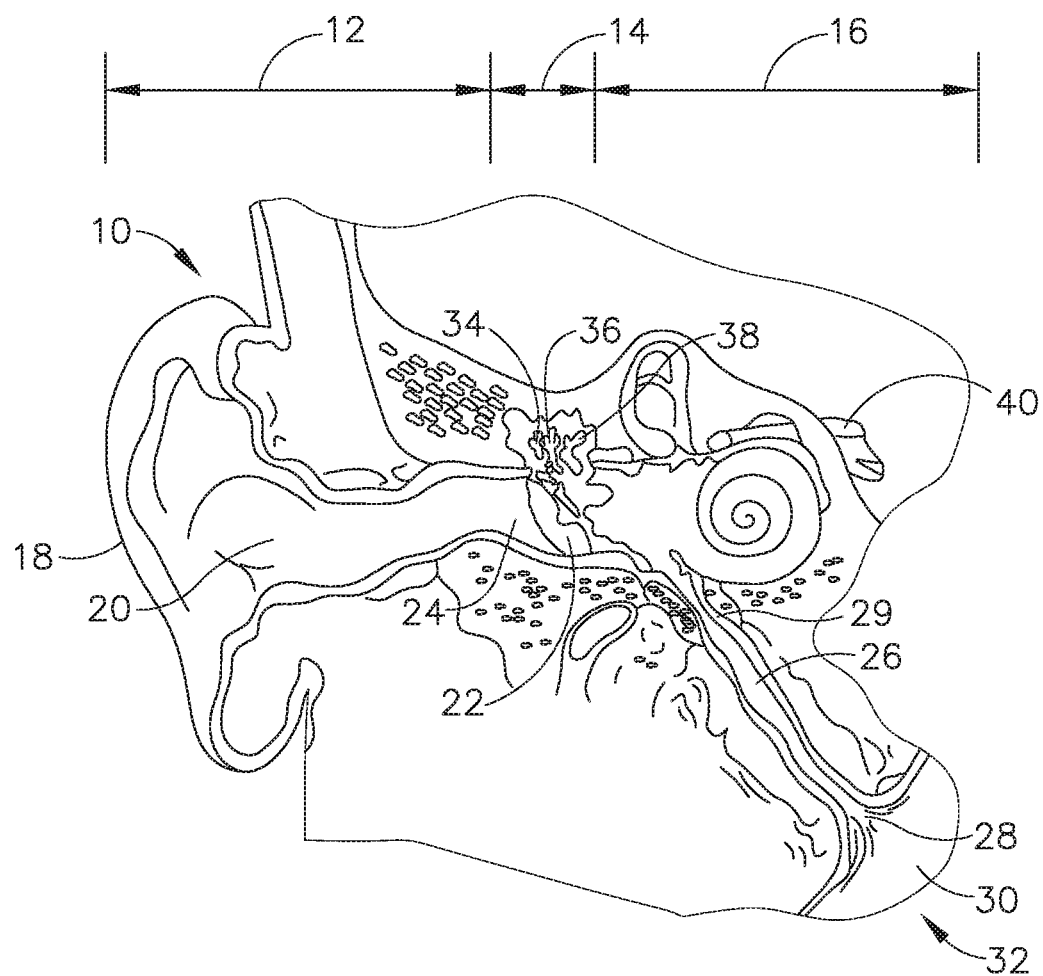
FIG. 1 depicts a cross-sectional view of an ear, with an inner, middle and outer ear portions and a Eustachian tube connecting the middle ear with a nasopharynx region.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview of Exemplary Eustachian Tube Treatment Procedures

Figure 2:
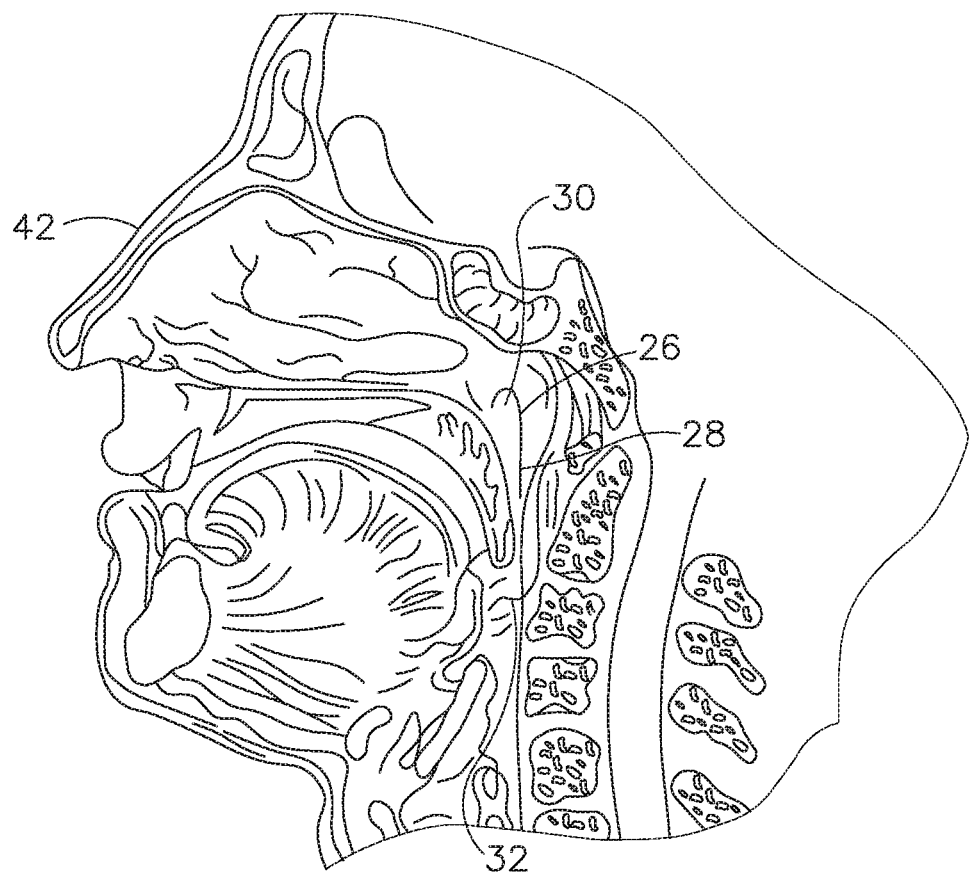
FIG. 2 depicts a cross-sectional view of a head, with the nasopharynx region of FIG. 1 fully visible.

FIGS. 1 and 2 show an ear (10) comprising three parts: an external ear (12), a middle ear (14) and an inner ear (16). External ear (12) includes an auricle (18) and an ear canal (20) that gather sound and direct it towards a tympanic membrane (22) (also referred to as the eardrum) located at an inner end (24) of the ear canal (20). Middle ear (14) lies between the external and inner ears (12) and (16) and is connected to the back of the throat by a Eustachian tube (26) which serves as a pressure equalizing valve between ear (10) and the sinuses. Eustachian tube (26) terminates in an opening or ostium (28) in the nasopharynx region (30) of the throat (32). In addition to tympanic membrane (22), middle ear (1.4) also includes three small ear bones (ossicles): a malleus (34) (hammer), an incus (36) (anvil) and a stapes (38) (stirrup). These bones (34, 36, 38) transmit sound vibrations to inner ear (16) and thereby act as a transformer, converting sound vibrations in canal (20) of external ear (12) into fluid waves in inner ear (16). These fluid waves stimulate several nerve endings (40) that, in turn, transmit sound energy to the brain where it is interpreted.

Eustachian tube (26) is shown as a narrow, two to two-and-a-half centimeter long channel, measured from ostium (28) to isthmus (29), connecting middle ear (14) with nasopharynx (30). Eustachian tube (26) functions as a pressure equalizing valve for middle ear (14), which is normally filled with air. Typically, Eustachian tube (26) opens for a fraction of a second periodically in response to swallowing or yawning. In so doing, it allows air into middle ear (14) to replace air that has been absorbed by the middle ear lining (mucous membrane) or to equalize pressure changes occurring on altitude changes. Anything that interferes with this periodic opening and closing of Eustachian tube (26) may result in hearing impairment or other ear symptoms.

Obstruction or blockage of Eustachian tube (26) results in a negative middle ear pressure (14), with retraction (sucking in) of tympanic membrane (22). In adults, this may be accompanied by some ear discomfort, a fullness or pressure feeling, and may result in a mild hearing impairment and/or head noise (tinnitus). There may be no symptoms in children. If the obstruction is prolonged, fluid may be drawn from the mucous membrane of middle ear (14), creating a condition referred to as serous otitis media (fluid in the middle ear). This may occur in children in connection with an upper respiratory infection and may account for hearing impairment associated with this condition.

A lining membrane (mucous membrane) of middle ear (14) and Eustachian tube (26) is connected with, and is the same as, the membrane of nose (42), sinuses (not shown) and throat (32). Infection of these areas results in mucous membrane swelling, which in turn may result in obstruction of Eustachian tube (26). This may ultimately result in acute or chronic serous otitis media, with fluid accumulating in middle ear (14). In the presence of bacteria, this fluid may become infected, leading to what may be referred to as an acute suppurative otitis media (infected or abscessed middle ear). When infection does not develop, the fluid remains until Eustachian tube (26) again begins to function normally, at which time the fluid is absorbed or drains down the Eustachian tube (26) into throat (32) through Eustachian tube ostium (28).

Chronic serous otitis media may result from longstanding Eustachian tube blockage, or from thickening of the fluid so that it cannot be absorbed or drained down Eustachian tube (26). Under some circumstances, this chronic condition may be associated with hearing impairment. There may also be recurrent ear pain. Fortunately, serous otitis media may persist for many years without producing any permanent damage to middle ear (14). The presence of fluid in middle ear (14), however, makes it very susceptible to recurrent acute infections. These recurrent infections may result in middle ear damage.

When Eustachian tube (26) contains a build-up of fluid, a number of things may occur. First, the body may absorb the air from middle ear (14), thus causing a vacuum to form. Such a vacuum may tend pull the lining membrane and ear drum (22) inwardly, causing pain. Next, the body may replace the vacuum with more fluid, which may tend to relieve pain, but the patient may experience a fullness sensation in ear (10). Treatment of this condition with antihistamines and decongestants can take many weeks to be fully effective. Finally, the fluid may become infected, which may be painful and may lead to other conditions associated with such an infection such as fever and/or hearing loss or degradation. If inner ear (14) is affected by such an infection, the patient may experience dizziness or disorientation— symptoms typically associated with the condition of vertigo.

Although the above described symptoms may be treated with antihistamines, decongestants, and antibiotics, such pharmaceuticals may be less desirable because they may not produce immediate resolution of symptoms caused by buildup of fluid in middle ear (14). Thus, immediate relief may be achieved by simply removing the fluid from Eustachian tube (26). Moreover, while administration of the pharmaceuticals described above may eventually resolve the infection, such treatment may not resolve the underlying issue of improper functioning of Eustachian tube (26). Accordingly, it may be desirable to perform surgical treatments of chronic serous otitis media to both achieve immediate relief of symptoms and to resolve any underling issues with Eustachian tube (26) function.

Figure 3:
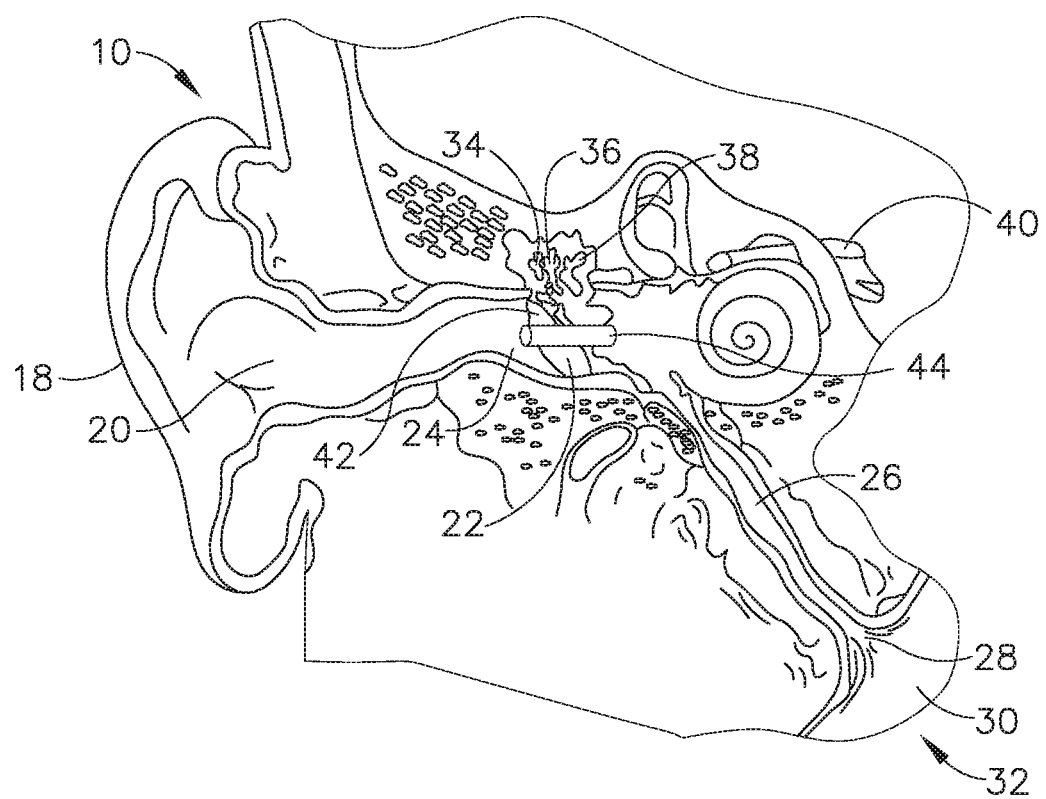
FIG. 3 depicts a cross-sectional view of the ear of FIG. 1, with a ventilation tube inserted within an incision in an eardrum.

FIG. 3 shows a myringotomy procedure, which may be performed to relieve fluid in middle ear (14). For instance, an incision (42) may be formed in tympanic membrane (22) to drain or remove fluid from middle ear (14). A hollow plastic tube (44) may be inserted and/or lodged in incision (42) to prevent incision (42) from self-sealing, thereby maintaining ventilation of middle ear (14) over an extended period of time. Thus during a treatment period, ventilation tube (44) temporarily takes the place of the Eustachian tube (26), performing the function of equalizing the pressure in middle ear (14). In some instances, the treatment period may last for a period of three to nine months. Such a period may permit the Eustachian tube (26) blockage to subside. After the treatment period, ventilation tube (44) may naturally dislodge and tympanic membrane (22) may self-seal. Alternatively, ventilation tribe (44) may be removed surgically by a medical professional. Regardless of how ventilation tube (44) is removed, Eustachian tube (26) may resume its typical function after the treatment period.

Figure 4:
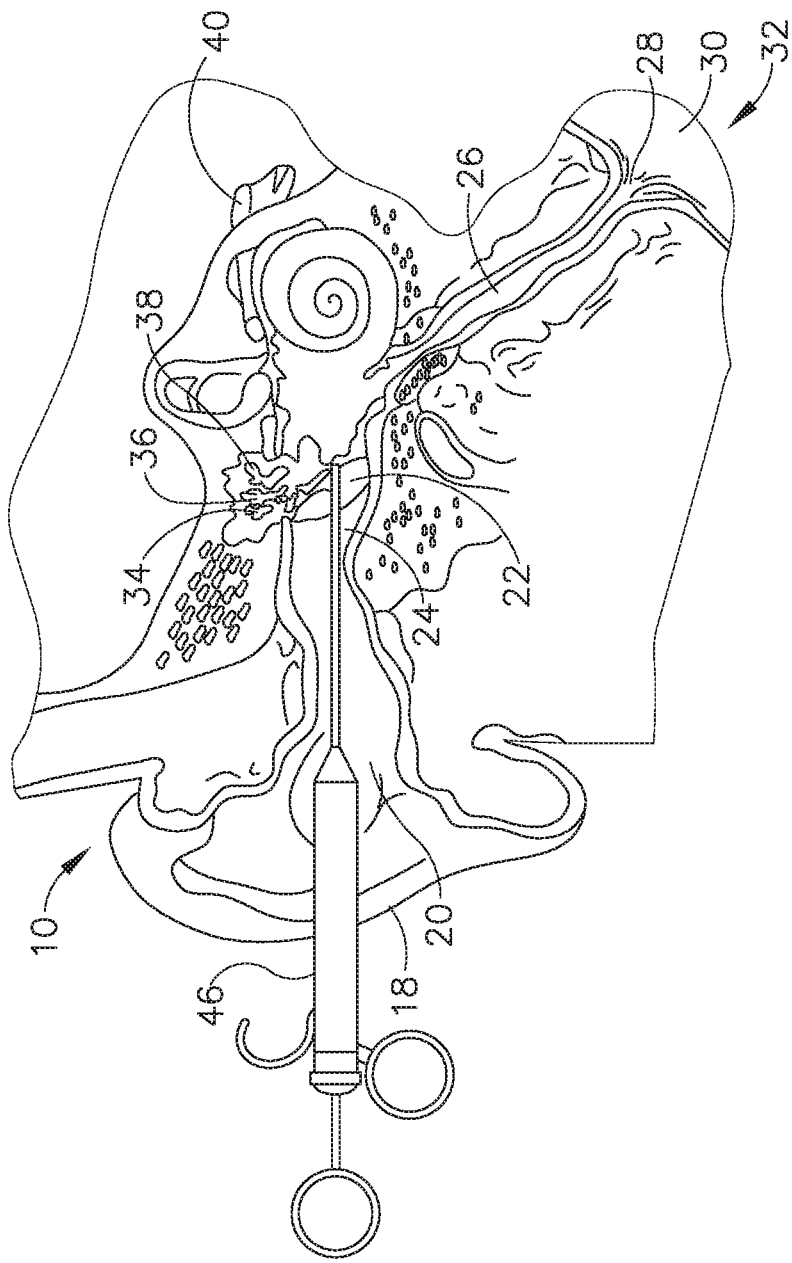
FIG. 4 depicts a cross-sectional view of the ear of FIG. 1, with a syringe perforating an eardrum.

FIG. 4 shows an exemplary alternative method of relieving middle ear (14) pressure. As can be seen, a hypodermic needle (46) is driven through tympanic membrane (22). Hypodermic needle (46) may then be used to manually withdraw fluid from middle ear (14). However, it should be understood that such a procedure shown in FIG. 4 may only result in removal of fluid from the upper portion of Eustachian tube (26). Thus, while effective at removing fluid from middle ear (14), some fluid may still remain when the procedure shown in FIG. 4 is used.

Although the procedures shown in FIGS. 3 and 4 may be effective in treating fluid buildup in middle ear (14), such procedures may be undesirable because both procedures involve a creating a perforation in tympanic membrane (22). Procedures leading to a perforation of tympanic membrane (22) may be undesirable because, in some instances, such a perforation could become permanent. Moreover, although the procedures described above may remove fluid from middle ear (14), the underlying problem of a blocked Eustachian tube (26) may remain.

Figure 5:
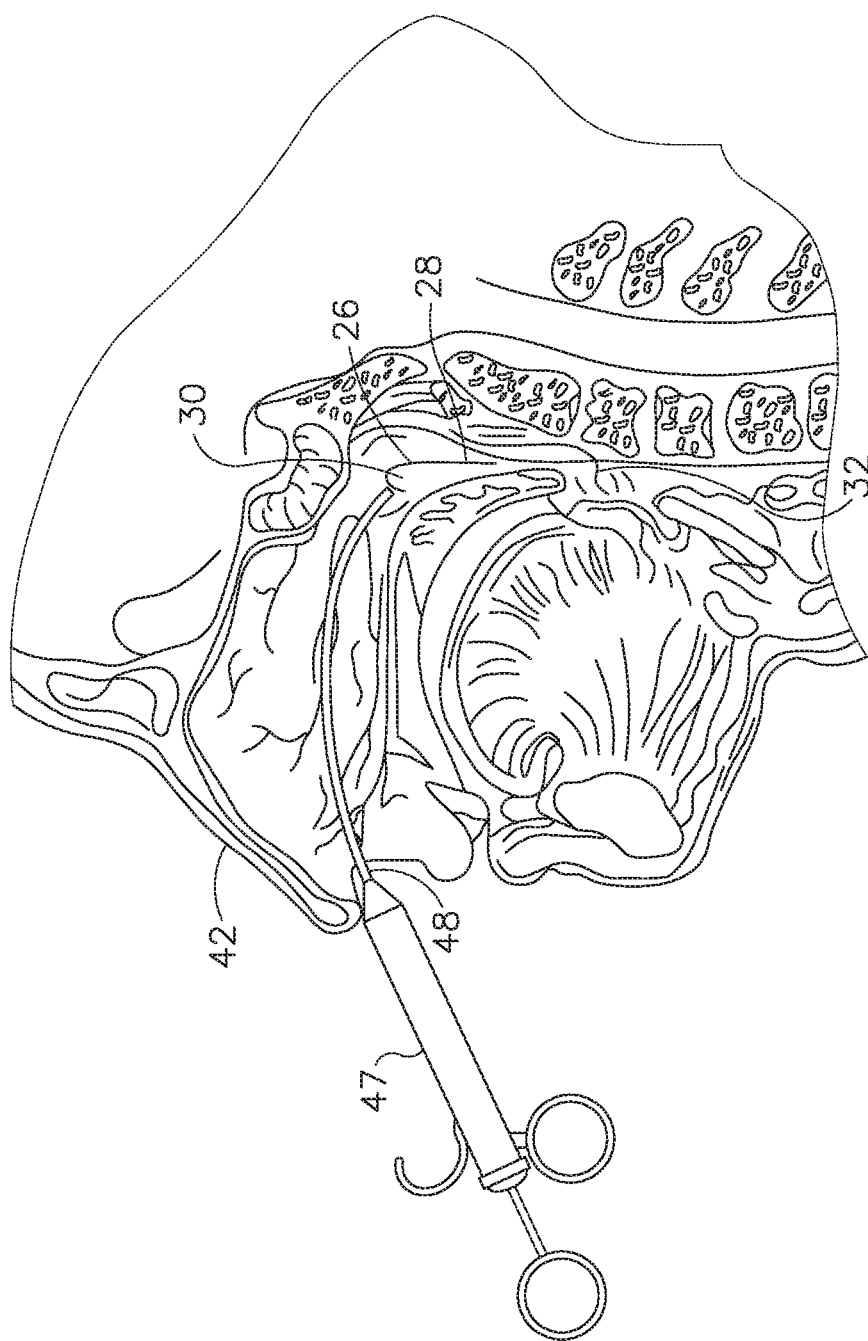
FIG. 5 depicts a cross-sectional view of the head of FIG. 2, with a syringe extending into the nasopharynx and abutting an ostium of the Eustachian tube.
Figure 6:
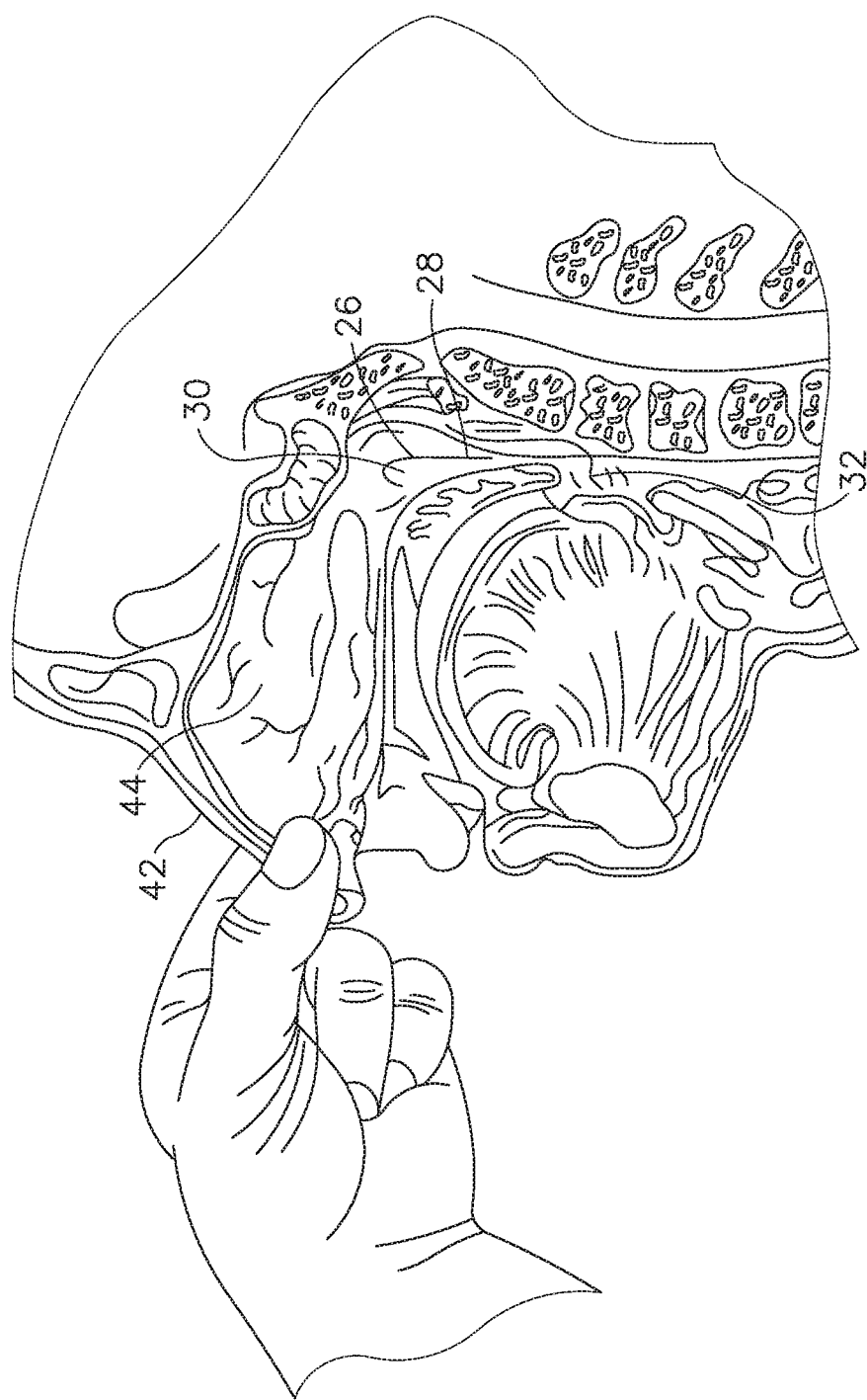
FIG. 6 depicts a cross-sectional view of the head of FIG. 2, with the nasalpharynx being manually plugged.

Another exemplary alternative procedure for treating fluid buildup in middle ear (14) is shown in FIGS. 5 and 6. As can best be seen in FIG. 5, a hypodermic syringe (47) with a flexible tip (48) is shown as being inserted into a nostril to position flexible tip (48) adjacent to ostium (28) of Eustachian tube (26) within nasopharynx (30). Syringe (47) may then be used to inject air or fluid through flexible tip (48) and into Eustachian tube (26). The force of the air traveling into Eustachian tube (26) may relieve congestion and reestablish middle ear (14) ventilation. In some circumstances this procedure may be referred to as politzerization. As shown in FIG. 6, such a procedure may optionally be performed while the nostrils are pinched shut with the patient simultaneously swallowing. Such a technique may aid in forcing air into Eustachian tube (26). While the procedure described above may be effective at opening Eustachian tube (26), it should be understood that the procedure does not necessarily clear fluid away from middle ear (14).

While not shown, it should be understood that a similar procedure to the politzerization procedure described above may be performed. Such a procedure may be referred to as a "valsalva" maneuver and may be accomplished by the patient forcibly blowing air into middle ear (14) while holding the nostrils closed. Such a procedure may also be colloquially referred to as "popping" the ear. While this procedure may open Eustachian tube (26), it should be understood that it may not necessarily lead to fluid being cleared from middle ear (14). Further procedures for treatment of fluid buildup in middle ear (14) are described in Ser. No. 14/317,269; issued as U.S. Pat. No. 10,350,396 on Jul. 16, 2019; and U.S. Pat. Pub. No. 2010/0274188, now abandoned, which are incorporated by reference herein.

II. Overview of Exemplary Eustachian Tube Dilation Systems

In some instances it may be desirable to dilate at least a portion of a Eustachian tube (26). For instance, as described above, in some circumstances a Eustachian tube (26) may become blocked or otherwise inflamed such that natural draining and ventilation of the middle ear (14) does not occur. In such circumstances, fluid buildup in the middle ear (14) may occur thus leading to chronic infection. While symptoms caused by such a blockage of the Eustachian tube (26) may be treated using procedures described above, treatment of the condition itself may still be desired. One such treatment may include the dilation of the Eustachian tube (26), thereby opening the Eustachian tube (26) to drain fluid from the middle ear (14) and restore natural functioning of the Eustachian tube (26).

The various examples described herein may dilate the Eustachian tube (26) through the use of a balloon catheter or other working instrument. By way of example only, a guide catheter may be inserted through a nostril of a patient and into the nasopharynx (30) to a position adjacent to the ostium (28) of the Eustachian tube (26). The balloon catheter may then be advanced relative to the guide catheter with the guide catheter directing the balloon catheter into the ostium (28) of the Eustachian tube (26). The balloon catheter may then be directed through the Eustachian tube (26) to a position where the balloon catheter may be expanded to dilate the Eustachian tube (26). Exemplary components that may be used to perform such a procedure are described in greater detail below.

A. Exemplary Guide Catheter

FIG. 7A shows an exemplary guide catheter (100) that may be used in a procedure to dilate a Eustachian tube (26) or other anatomical passageway. As can be seen, guide catheter (100) comprises an elongate tubular shaft (102) including a proximal end (104) and a distal end (106) and a lumen (108) extending therebetween. It should be understood that guide catheter (100) may have any suitable length, diameter, angle of bend, and location of bend along the length of catheter (100), to facilitate accessing the ostium (28) of the Eustachian tube (26). By way of example only, in some examples guide catheter (100) may have a length between about 8 cm and about 20 cm. In other examples, guide catheter (100) may have a length between about 10 cm and about 15 cm. In still other examples, guide catheter (100) may have a length of about 11 cm. Of course, any other suitable dimensions may be used.

FIG. 7B shows a cross-section of tubular shaft (102). As can be seen, shaft (102) has an outer shaft tube (110), an inner shaft tube (112) and a lumen (108). Outer shaft tube (110) may be constructed of a stiff material such as stainless steel, nitinol, hard plastic, etc. Inner tube shaft (112) may be constructed of a relatively more flexible material such as a polymeric material including but not limited to nylon. In some examples, inner shaft tube (112) may further include a PTFE liner. Lumen (108) is generally configured such that a balloon dilation catheter (200), described below, may be slidably disposed within lumen (108). Lumen (108) of the present example has a diameter of between about 2 mm and 3 mm. In other examples, lumen (108) may have a diameter of between 2.5 mm and 2.6 mm. Again, any other suitable dimensions may be used. In the present example, the combination of guide catheter (100) and balloon catheter (200) form a compact system that is configured for one-handed operation.

FIG. 8 shows a detailed view of distal portion (120) of guide catheter (100). Distal portion (120) of the present example includes a bend (122) with an angle between about 45 degrees and about 65 degrees. In other examples, bend (122) may range between about 50 degrees and 60 degrees. In still other examples, bend (122) may be about 55 degrees. Alternatively, any other suitable bend angle may be used. Regardless of the particular bend angle of bend (122) it should be understood that bend (122) is configured to facilitate access into a Eustachian tube (26) from the nasopharynx (30) of a patient, as will be described in greater detail below.

Distal portion (120) of guide catheter (1100) further includes a distal tip (124). Distal tip (124) comprises a transparent material such as a polymer including, but not limited to, nylon, polyether block amides (e.g., PEBAX® by Arkema), and/or PTFE. As will be understood, the transparent nature of distal tip (124) may permit dilation catheter (200) to be visible through distal tip (124). In addition to distal tip (124) being comprised of a transparent material, such a material may also be configured to be more flexible relative to the material of elongate shaft (102) such that distal tip (124) is atraumatic in character. In other examples, distal tip (124) may be infused with 20% barium sulfate or other similar radiopaque materials, thereby making distal tip (124) visible under x-ray or other radiographic visualization. Other suitable materials that may be used to form distal tip (124) (or that may be otherwise incorporated into distal tip (124)) will be apparent to those of ordinary skill in the art in view of the teachings herein.

Referring again to FIG. 7A, a proximal portion (130) of guide catheter (100) includes a proximal hub (132) to aid in insertion of balloon dilation catheter (200) into the Eustachian Tube (26). Hub (132) has a larger diameter proximal end (134) and a smaller diameter middle section (136) to facilitate stabilization of guide catheter (100) in the nose (42), rotation of guide catheter (100) and insertion of balloon dilation catheter (200) as will be described in further detail below. Hub (132) is ergonomically designed for insertion, location and rotation with slight manipulations with one hand.

B. Exemplary Dilation Catheter

FIG. 9A shows dilation catheter (200), which is generally insertable into lumen (108) of guide catheter (100) for dilation of a Eustachian tube (26). Dilation catheter (200) comprises an elongate shaft (202) having a proximal end (214) and a distal end (218). Dilation catheter (200) further includes a balloon (204) located proximal to a distal tip (212) of distal end (218). Balloon (204) comprises a polymer balloon and may be compliant, semi-compliant, or non-compliant. In some examples, balloon (204) may comprise a suitable non-compliant material such as polyethylene terepthalate (PET), PEBAX®, nylon, or the like. Balloon (204) may be of any diameter suitable to dilate a Eustachian tube (26). For instance, in some examples balloon (204) may be of an inflated diameter ranging between about 2 mm to about 8 mm. In other examples, the inflated diameter of balloon (204) may range between about 5 mm and 6 mm. Alternatively, any other suitable diameters may be provided. Balloon (204) may also be of any suitable working length. For instance, in some examples balloon (204) may have a working length between about 12 mm and 24 mm. Balloon (204) may comprise any suitable combination of diameter and working length, as will be apparent to those of ordinary skill in the art in view of the teachings herein. Some merely exemplary combinations may include, for example, 2 mm×12 mm, 3.5 mm×12 mm, 5 mm×16 mm, 5 mm×24 mm, 6 mm×16 mm, 6 mm×20, 6 mm×24 mm, 7 mm×16 mm, and 7 mm×24 mm.

Balloon (204) may be expanded to dilate the Eustachian tube (26) after it is placed in a desired location therein. For example, the Eustachian tube (26) includes a pharyngeal ostium (28), and dilation catheter (200) may be advanced to position balloon (204) in the pharyngeal ostium (28). An endoscope may be used to assist in positioning balloon dilation catheter (200). The endoscope may be advanced through the nasal passage to view dilation catheter (200). A marker (208) on elongate shaft (202) of dilation catheter (200) can be viewed from the endoscope to approximate a location of balloon (204) relative to the opening of the Eustachian tube (26) based on a distance of marker (208)

from a proximal end of balloon (204). Accordingly, dilation catheter (200) can be moved to place marker (208) in a desired location before expansion of balloon (204) in the Eustachian tube (26). Although only marker (208) is shown, it should be understood that in other examples dilation catheter (200) may include any suitable number of markers positioned at various locations along the length of dilation catheter (200).

Dilation catheter (200) further includes an actuator (210). Actuator (210) has a proximal side (220) and a distal side (222). In the present example, actuator (210) is secured to elongate shaft (202) of dilation catheter (200) by adhesive bonding, although any other suitable means of securing actuator (210) may be used. Actuator (210) is configured to allow for single-handed manipulation of dilation catheter (200). Although actuator (210) may be used in any suitable way, in one merely exemplary use actuator (210) is gripped with a thumb and index finger of an operator while any remaining fingers of the operator may be free to grip the endoscope or any other instrument. Actuator (210) thus allows for easy, ergonomic one-handed advancement of balloon dilation catheter (200) through guide catheter (100) and into the Eustachian Tube (26).

Elongate shaft (202) comprises a proximal portion (238) that is proximal to actuator (210). Elongate shaft (202) further comprises a first distal portion (240) and a second distal portion (250) that are distal to actuator (210). First distal portion (240) is sufficiently stiff to be guided through the nasal cavity and into the Eustachian Tube (26) and is constructed of stainless steel (or other biocompatible material) and preferably includes a stainless steel hypotube. Proximal portion (238) and second distal portion (250), on the other hand, are relatively flexible and are simply constructed of a polymeric material including but not limited to PEBAX® that extends through the length of elongate shaft (202). While first distal portion (240) is of a stiffness such that actuator (210) may guide dilation catheter (200) though a nasal cavity and into a Eustachian tube (26), second distal portion (250) is sufficiently flexible to permit balloon (204) to flex into position as dilation catheter (200) is advanced through a nasal cavity and into a Eustachian tube (26). Proximal portion (238) is similarly flexible such that elongate shaft (202) will not interfere with the endoscope as actuator (210) is used to advance dilation catheter (200).

FIG. 9B shows a cross-section of shaft (202). As can be seen, shaft (202) comprises an inflation lumen (232), and a working lumen (234). Inflation lumen (232) is in communication with the interior of balloon (204) distally, and an inflation port (230) proximally. Accordingly, inflation lumen (232) provides a passage for fluid communication to balloon (204) such that balloon (204) may be inflated by connecting an inflation device (not shown) to inflation port (230) to thereby inject fluid into balloon (204).

Working lumen (234) extends longitudinally through shaft (202) from distal (218) end to proximal end (214). Working lumen (234) is configured to receive various other instruments such a guide wire that may be optionally used in conjunction with dilation catheter (200). Additionally, working lumen (234) provides the function of relieving pressure from a Eustachian tube (26) as it is being dilated. In particular, because balloon (204) blocks the Eustachian tube (26) and the opposite end of the Eustachian tube (26) is sealed by the tympanic membrane (22), pressure may potentially build in the space between balloon (204) and the tympanic membrane (22). However, because working lumen (234) extends through shaft (202) and out of the distal end of shaft (202), working lumen (234) provides ventilation of the space between balloon (204) and the tympanic membrane (22), thereby preventing any potential pressure buildup, particularly when balloon (204) is expanded and occupies volume that had previously been occupied by air in the Eustachian tube (26).

As can best be seen in FIG. 10, distal end (218) of dilation catheter (200) further includes a tip (212) and a flexible shaft portion (250). Tip (212) and flexible shaft portion (250) are constructed of a polymeric material including but not limited to PEBAX®. In the present example, PEBAX® extends from the distal end of elongate shaft (202) to the proximal end of balloon (204). Tip (212) of the present example is bulbous in shape to thereby provide atraumatic properties. By way of example only, tip (212) is about 1.5 mm to about 2 mm in length with a maximum outer diameter of between about 2 mm and 3 mm. It should be understood that the shape of tip (212), including its smoothness and roundness, is configured to facilitate advancement of dilation catheter (200) by allowing the distal end of dilation catheter (200) to glide smoothly through a Eustachian tube (26). It should further be understood that tip (212) also acts as a safety stop. For instance, an isthmus (29) of a Eustachian tube (26) is generally about 1 mm in diameter. However, as described above, tip (212) is generally larger in diameter than 1 mm. Accordingly, tip (212) is sized to prevent dilation catheter (200) from passing through the isthmus (29) and into the middle ear (14).

C. Exemplary Use of Exemplary Guide Catheter and Dilation Catheter Assembly

In an exemplary use, guide catheter (100) may be initially advanced into a nostril and through a nasal cavity to a position distal end (106) of guide catheter (100) at, or near the ostium (28) of the Eustachian tube (26). In one embodiment, guide catheter (100) may be passed through a nostril to a Eustachian tube (26) on the ipsilateral (same side) of a head. Alternatively, guide catheter (100) may be passed through a nostril to a Eustachian tube (26) on the contralateral (opposite side) of a head. It should be understood that although guide catheter (100) is described as being used to access a Eustachian tube (26), in other examples a guiding element such as a guidewire or illuminating fiber may be used to assist with the positioning of guide catheter (100).

After guide catheter (100) is in a desired position, dilation catheter (200) is advanced relative to guide catheter (100). In the present example, dilation catheter (200) is advanced through guide catheter (100), although it should be understood that in other examples, dilation catheter (200) may instead be advanced over guide catheter (100). Regardless, dilation catheter (200) is advanced distally of guide catheter (100) to position balloon (204) of dilation catheter (200) within a Eustachian tube (26). To advance and position dilation catheter (200) an operator may place a thumb on proximal side (220) of actuator (210) or within both sides (220, 222) of actuator (210). The thumb may be used to slide dilation catheter (200) through guide catheter (100). Alternatively, the operator may grasp proximal hub (132) of guide catheter (100) and use an index finger placed on proximal side (220) of actuator (210) or in between distal side (222) and proximal side (220) of actuator (210) to advance dilation catheter (200). As dilation catheter (200) is advanced, the larger diameter tip (212) prevents dilation catheter (200) from advancing too far through Eustachian tube (26), as described above. Further, distal side (222) of actuator (210) will contact proximal end (104) of guide catheter (100), such that dilation catheter (200) is only permitted to advance a certain maximum distance relative to guide catheter (100).

Accordingly, actuator (210) also may prevent dilation catheter (200) from being advanced too far into a Eustachian tube (26).

Once dilation catheter (200) is positioned at a desired position within a Eustachian tube (26), balloon (204) may be inflated and held in location while in an expanded state for an extended period of time (e.g. several seconds or minutes). Dilation catheter (200) may also deliver a substance to the Eustachian tube (26), such as one or more of the therapeutic or diagnostic agents described herein. Balloon (204) may also carry an expandable stent for delivery into the Eustachian tube (26) upon expansion of balloon (204). Dilation catheter (200) and guide catheter (100) may be removed from the patient after balloon (204) has been deflated/unexpanded. The Eustachian tube (26) will resume functioning, normally opening and closing to equalize atmospheric pressure in the middle ear and protect the middle ear from unwanted pressure fluctuations and loud sounds.

In an alternative use, dilation catheter (200) may be advanced into a nostril of a patent with guide catheter (100) omitted. In such a use, dilation catheter (200) may be used with or without a guide device such as a guide wire or illuminating fiber. Regardless, an operator may advance dilation catheter (200) though a nostril of a patient until proximal side (220) of actuator (210) is adjacent to the patient's nostril. Distal side (222) of actuator (210) will contact patient's nostril, thereby preventing further advancement of dilation catheter (200). Thus even when dilation catheter (200) is used without guide catheter (100), actuator (210) may prevent dilation catheter (200) from being advanced too far within a Eustachian tube (26).

Working lumen (234) permits the optional injection of water, medicament, or even the introduction of a guidewire through injection port (236) at proximal end (216) of proximal connector (206). In order to ensure that inflation port (230) is used for balloon inflation only, inflation port (230) and injection port (236) may optionally comprise different type connectors. For example, inflation port (230) may comprise a female connector whereas injection port (236) comprises a male connector or vice versa. Alternatively, injection port (236) may comprise a right-handed thread connected and inflation port (230) may comprise a left-handed thread connector or vice versa. It may be desirable to inject solutions containing contrast agents, pharmaceutically acceptable salt or dosage form of an antimicrobial agent (e.g. antibiotic, antiviral, anti-parasitic, antifungal, etc.), an anesthetic agent with or without a vasoconstriction agent (e.g. Xylocaine with or without epinephrine, Tetracaine with or without epinephrine, etc.), an analgesic agent, a corticosteroid or other anti-inflammatory (e.g. an NSAID), a decongestant (e.g. vasoconstrictor), a mucus thinning agent (e.g. an expectorant or mucolytic), a surfactant, an agent that prevents or modifies an allergic response (e.g. an antihistamine, cytokine inhibitor, leucotriene inhibitor, IgE inhibitor, immunomodulator), an allergen or another substance that causes secretion of mucous by tissues, hemostatic agents to stop bleeding, antiproliferative agents, cytotoxic agents (e.g. alcohol), biological agents such as protein molecules, stem cells, genes or gene therapy preparations, or the like.

Some nonlimiting examples of antimicrobial agents that may be used include acyclovir, amantadine, aminoglycosides (e.g., amikacin, gentamicin and tobramycin), amoxicillinklavulanate, amphotericin B, ampicilin ampicillintsulbactam, atovaquone, azithromycin, cefazolin, cefepime, cefotaxime, cefotetan, cefpodoxime, ceflazidime, ceflizoxime, ceftriaxone, cefuroxime, cefuroxime axetil, cephalexin, chloramphenicol, clotrimazole, ciprofloxacin, clarithromycin, clindamycin, dapsone, dicloxacillin, doxycycline, erythromycin, fluconazole, foscarnet, ganciclovir, atifloxacin, imipenemlcilastatin, isoniazid, itraconazole, ketoconazole, metronidazole, nafcillin, nystatin, penicillin, penicillin G, pentamidine, piperacillinitazobactam, rifampin, quinupristindalfopristin, ticarcillinlclavulanate, trimethoprimisulfamethoxazole, valacyclovir, vancomycin, mafenide, silver sulfadiazine, mupirocin (e.g., Bactroban, Glaxo SmithKline, Research Triangle Park, N.C.), nystatin, triamcinolonelnystatin, clotrimazolelbetamethasone, clotrimazole, ketoconazole, butoconazole, miconazole, tioconazole, detergent-like chemicals that disrupt or disable microbes (e.g., nonoxynol-9, octoxynol-9, benzalkonium chloride, menfegol, and N-docasanol); chemicals that block microbial attachment to target cells and/or inhibits entry of infectious pathogens (e.g., sulphated and sulphonated polymers such as PC-515 (carrageenan), Pro-2000, and Dextrin 2 Sulphate); antiretroviral agents (e.g., PMPA gel) that prevent retroviruses from replicating in the cells; genetically engineered or naturally occurring antibodies that combat pathogens such as anti-viral antibodies genetically engineered from plants known as "plantibodies;" agents which change the condition of the tissue to make it hostile to the pathogen (such as substances which alter mucosal pH (e.g., Buffer Gel and Acid form); non-pathogenic or "friendly" microbes that cause the production of hydrogen peroxide or other substances that kill or inhibit the growth of pathogenic microbes (e.g., lactobacillus); antimicrobial proteins or peptides such as those described in U.S. Pat. No. 6,716,813, entitled "Use of Antimicrobial Proteins and Peptides for the Treatment of Otitis Media and Paranasal Sinusitis," issued Apr. 6, 2004, the disclosure of which is incorporated by reference herein, or antimicrobial metals (e.g., colloidal silver).

Additionally or alternatively, in some applications where it is desired to treat or prevent inflammation the substances delivered may include various steroids or other anti-inflammatory agents (e.g., nonsteroidal anti-inflammatory agents or NSAIDS), analgesic agents or antipyretic agents. For example, corticosteroids that have previously administered by intranasal 10 administration may be used, such as beclomethasone (Vancenase® or Beconase), flunisolide (Nasalid®), fluticasone proprionate (Flonase®), triamcinolone acetonide (Nasacort®), budesonide (Rhinocort Aqua®), loterednol etabonate (Locort) and mornetasone (Nasonex®). Other salt forms of the aforementioned corticosteroids may also be used. Also, other non-limiting examples of steroids that may be useable include but are not limited to aclometasone, desonide, hydrocortisone, betamethasone, clocortolone, desoximetasone, fluocinolone, flurandrenolide, mometasone, prednicarbate; amcinonide, desoximetasone, diflorasone, fluocinolone, fluocinonide, halcinonide, clobetasol, augmented betamethasone, diflorasone, halobetasol, prednisone, dexamethasone and methylprednisolone. Other anti-inflammatory, analgesic or antipyretic agents that may be used include the nonselective COX inhibitors (e.g., salicylic acid derivatives, aspirin, sodium salicylate, choline magnesium trisalicylate, salsalate, diflunisal sulfasalazine and olsalazine; para-aminophenol derivatives such as acetaminophen; indole and indene acetic acids such as indomethacin and sulindac; heteroaryl acetic acids such as tolmetin, dicofenac and ketorolac; aryipmpionic acids such as ibuprofen, naproxen, flurbiprofen, ketoprofen, fenoprofen and oxaprozin; anthranilic acids (fenamates) such as mefenamic acid and meloxicam; enolic acids such as the oxicams (piroxicam, meloxicam) and alkanones such as nabumetone) and Selective COX-2

Inhibitors (e.g., diaryl-substituted furanoses such as rofecoxib; diaryl-substituted pyrazoles such as celecoxib; indole acetic acids such as etodolac and sulfonanilides such as mmesulide).

Additionally or alternatively, in some applications, such as those where it is desired to treat or prevent an allergic or immune response and/or cellular proliferation, the substances delivered may include: various cytokine inhibitors such as humanized anti-cytokine antibodies, anti-cytokine receptor antibodies, recombinant (new cell resulting from genetic recombination) antagonists, or soluble receptors; various leucotriene modifiers such as zafirlukast, montelukast and zileuton; immunoglobutin E (IgE) inhibitors such as Omalizumab (an anti-IgE monoclonal antibody formerly called rhu Mab-E25) and secretory leukocyte protease inhibitor); and SYK Kinase inhibitors such as an agent designated as "R-112" manufactured by Rigel Pharmaceuticals, Inc. South San Francisco, Calif.

Additionally or alternatively, in some applications, such as those where it is desired to shrink mucosal tissue, cause decongestion, or effect hemostasis, the substances delivered may include various vasoconstrictors for decongestant and or hemostatic purposes including but not limited to pseudoephedrine, xylometazoline, oxymetazoline, phenylephrine, epinephrine, etc.

Additionally or alternatively, in some applications, such as those where it is desired to facilitate the flow of mucous, the substances delivered may include various mucolytics or other agents that modify the viscosity or consistency of mucous or mucoid secretions, including but not limited to acetylcysteine. In one particular embodiment, the substance delivered may comprise a combination of an anti-inflammatory agent (e.g. a steroid or an NSAID) and a mucolytic agent.

Additionally or alternatively, in some applications such as those where it is desired to prevent or deter histamine release, the substances delivered may include various mast cell stabilizers or drugs which prevent the release of histamine such as cromolyn (e.g., Nasal Chroma) and nedocromil.

Additionally or alternatively, in some applications such as those where it is desired to prevent or inhibit the effect of histamine, the substances delivered may include various antihistamines such as azelastine (e.g., Astylin) diphenhydramine, loratidine, etc.

Additionally or alternatively, in some embodiments such as those where it is desired to dissolve, degrade, cut, break or remodel bone or cartilage, the substances delivered may include substances that weaken or modify bone and/or cartilage to facilitate other procedures wherein bone or cartilage is remodeled, reshaped, broken or removed. One example of such an agent would be a calcium chelator such as EDTA that could be injected or delivered in a substance delivery implant next to a region of bone that is to be remodeled or modified. Another example would be a preparation consisting of or containing bone degrading cells such as osteoclasts. Other examples would include various enzymes of material that may soften or break down components of bone or cartilage such as collagenase (CG), trypsin, trypsinlLEDTA, hyaluronidase, and tosyllysylchloromethane (TLCM).

Additionally or alternatively, in some applications such as those wherein it is desired to treat a tumor or cancerous lesion, the substances delivered may include antitumor agents (e.g., cancer chemotherapeutic agents, biological response modifiers, vascularization inhibitors, hormone receptor blockers, cryotherapeutic agents or other agents that destroy or inhibit neoplasia or tumorigenesis) such as; alkylating agents or other agents which directly kill cancer cells by attacking their DNA (e.g., cycophosphamide, isophosphamide), nitrosoureas or other agents which kill cancer cells by inhibiting changes necessary for cellular DNA repair (e.g., carmustine (BCNU) and lomustine (CCNU)), antimetabolites and other agents that block cancer cell growth by interfering with certain cell functions, usually DNA synthesis (e.g., 6 mercaptopurine and 5-fluorouracil (5FU), antitumor antibiotics and other compounds that act by binding or intercalating DNA and preventing RNA synthesis (e.g., doxorubicin, daunorubicin, epirubicin, idarubicin, mitomycin-C and bleomycin) plant (vinca) alkaloids and other antitumor agents derived from plants (e.g., vincristine and vinblastine), steroid hormones, hormone inhibitors, hormone receptor antagonists and other agents which affect the growth of hormone-responsive cancers (e.g., tamoxifen, herceptin, aromatase inhibitors such as aminoglutethamide and formestane, trriazole inhibitors such as letrozole and anastrazole, steroidal inhibitors such as exemestane), antiangiogenic proteins, small molecules, gene therapies and/or other agents that inhibit angiogenesis or vascularization of tumors (e.g., meth-1, meth-2, thalidomide), bevacizumab (Avastin), squalamine, endostatin, angiostatin, Angiozyme, AE-941 (Neovastat), CC-5013 (Revimid), medi-522 (Vitaxin), 2-methoxyestradiol (2ME2, Panzem), carboxyamidotriazole (CAI), combretastatin A4 prodrug (CA4P), SU6668, SU11248, BMS-275291, COL-3, EMI) 121974, 1MC-IC11, 1M862, TNP-470, celecoxib (Celebrex), rofecoxib (Vioxx), interferon alpha, interleukin-12 (IL-12) or any of the compounds identified in Science Vol. 289, Pages 1197-1201 (Aug. 17, 2000) which is expressly incorporated herein by reference, biological response modifiers (e.g., interferon, bacillus calmetteguerin (BCG), monoclonal antibodies, interluken 2, granulocyte colony stimulating factor (GCSE), etc.), PGDF receptor antagonists, herceptin, asparaginase, busulphan, carboplatin, cisplatin, carmustine, cchlorambucil, cytarabine, dacarbazine, etoposide, flucarbazine, fluorouracil, gemcitabine, hydroxyurea, ifosphamide, irinotecan, lomustine, melphalan, mercaptopurine, methotrexate, thioguanine, thiotepa, tomudex, topotecan, treosulfan, vinblastine, vincristine, mitoazitrone, oxaliplatin, procarbazine, streptocin, taxol, taxotere, analogslcongeners and derivatives of such compounds as well as other antitumor agents not listed here.

Additionally or alternatively, in some applications such as those where it is desired to grow new cells or to modify existing cells, the substances delivered may include cells (mucosal cells, fibroblasts, stem cells or genetically engineered cells) as well as genes and gene delivery vehicles like plasmids, adenoviral vectors or naked DNA, mRNA, etc. injected with genes that code for anti-inflammatory substances, etc., and, as mentioned above, osteoclasts that modify or soften bone when so desired, cells that participate in or effect mucogenesis or ciliagenesis, etc.

In some instances, a local anesthetic, such as Lidocaine is injected through working lumen (234) prior to dilation of the Eustachian tube (26). Working lumen (234) can be used for venting during dilation so that pressure in the middle ear (14) does not increase or decrease.

D. Exemplary Alternative Guide Catheter

Figure 11:
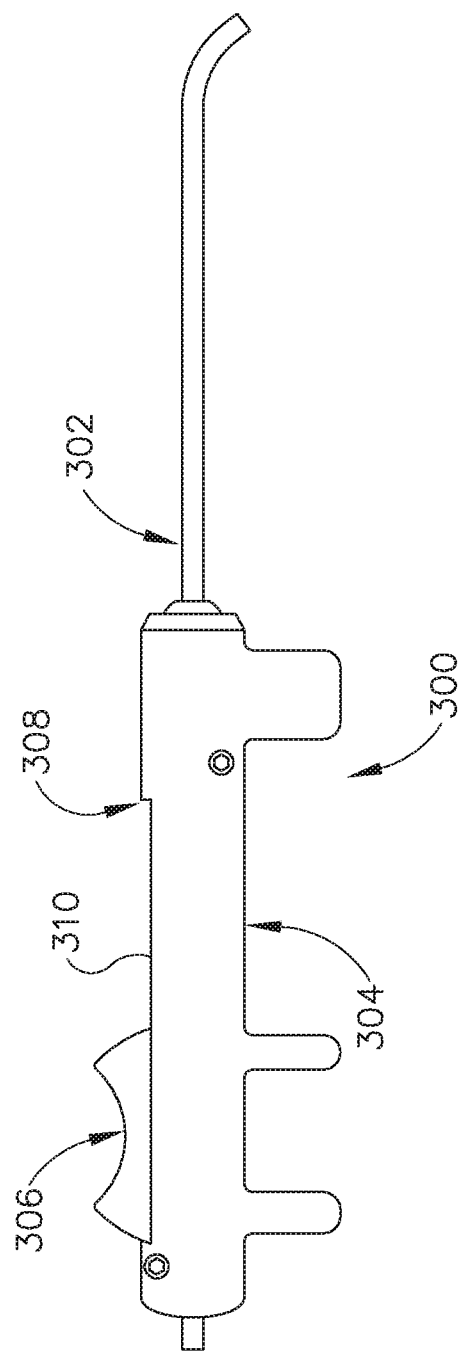
FIG. 11 depicts a side elevational view of an exemplary alternative guide catheter.

FIG. 11 shows an exemplary alternative guide catheter (300), which may be used in lieu of guide catheter (100) described above. Guide catheter (300) is substantially the same as guide catheter (100), except as where otherwise noted herein. Guide catheter (300) of the present example comprises an elongate shaft (302), which is substantially the same as shaft (102) described above. Guide catheter (300) further comprises a handle (304), which is similar in function to proximal hub (130) of guide catheter (100). Handle (304), unlike proximal hub (130), comprises an actuator (306) that may be attached to dilation catheter (200) such that actuator (306) may be used to advance dilation catheter (200). As can be seen, handle (304) includes an elongate track (310), which slidably supports actuator (306), thereby permitting actuator (306) to slide longitudinally relative to handle (304) to thereby advance and retract dilation catheter (200) relative to guide catheter (300). Track (310) further includes a stop (308), which may prevent over insertion of dilation catheter (200) into a Eustachian tube (26).

In an exemplary use of guide catheter (300), guide catheter (300) is gripped by an operator using a handle (304) and shaft (302) is inserted into a nostril of a patient. Because actuator (306) of guide catheter (300) may be attached to dilation catheter (200), it should be understood that as guide catheter (300) is inserted into the nostril, dilation catheter (200) may likewise be inserted into the nostril. However, dilation catheter (200) may remain within shaft (302) until an operator desires to advance dilation catheter (200).

Guide catheter (300) may be advanced within a nostril of the patient until the distal end of shaft is adjacent to an ostium (28) of a Eustachian tube (26). At such a point, an operator may begin advancing dilation catheter (200) separately from guide catheter (300). To engage in such advancement, the operator may slide actuator (306) along track (310). Actuator (306) may be advanced until either dilation catheter (200) is advanced to a desired position or until actuator (306) reaches stop (308). Regardless, once dilation catheter (200) is positioned at a desired position in a Eustachian tube (26), the operator may expand balloon (204) of dilation catheter (200) to dilate the Eustachian tube (26) similarly as described above.

III. Exemplary Eustachian Tube Dilation Systems with Integral Camera

In some instances it may be desirable to include optical sensors and/or light emitters in a guide catheter similar to catheter (100) described above. For instance, in some patients the particular autonomy of the patient may make maneuvering an endoscope and a guide catheter together within the nostril of the patient challenging. Thus there may be a need for guide catheters that can provide visualization, guidance, and dilation without requiring a separate endoscope. In other instances, a patient's anatomy may permit use of an endoscope and a guide catheter simultaneously, yet the field of view of the endoscope may be limited by the patient's anatomy or the instruments themselves. Accordingly, the instruments described below include one or more integral optical sensors and/or light emitting features. It should be understood that while the instruments described below are discussed in the context of being usable with each other, each individual instrument may instead be used in conjunction with any instruments described above in addition to, or in lieu of similar instruments.

A. Exemplary Guide Catheter with Integral Camera

Figure 12:
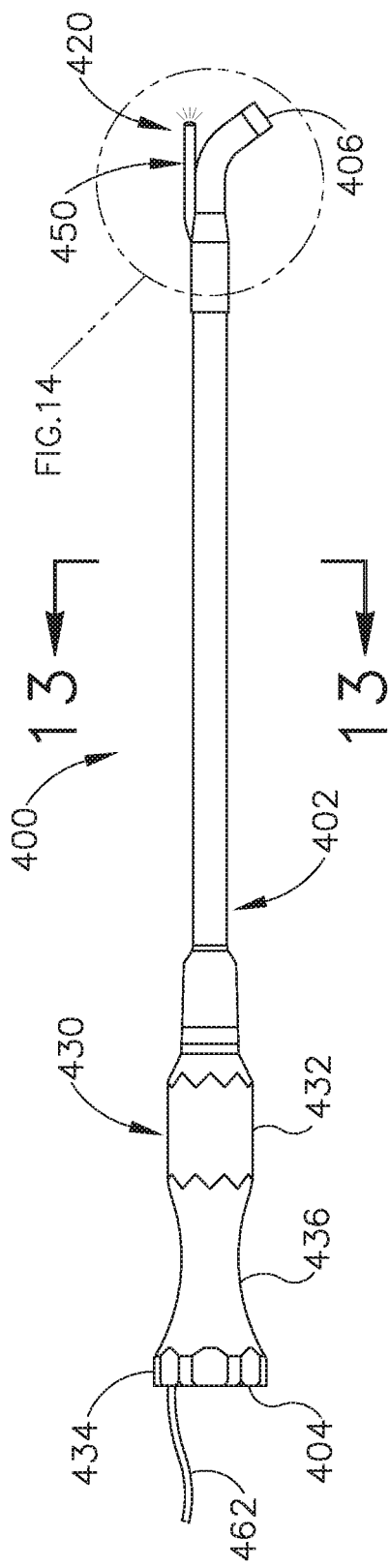
FIG. 12 depicts side elevational view of another exemplary alternative guide catheter.

FIG. 12 shows an exemplary guide catheter (400) that may be used in a procedure to dilate a Eustachian tube (26) or other anatomical passageway. Guide catheter (400) is substantially the same as guide catheter (100) described above, expect for as otherwise noted herein. For instance, guide catheter (400) comprises an elongate tubular shaft (402) including a proximal end (404) and a distal end (406) and a lumen (408) extending therebetween. It should be understood that, like guide catheter (100), guide catheter (400) may have any suitable length, diameter, angle of bend, and location of bend along the length of catheter (400), to facilitate accessing the opening (28) of a Eustachian tube (26).

Figure 13:
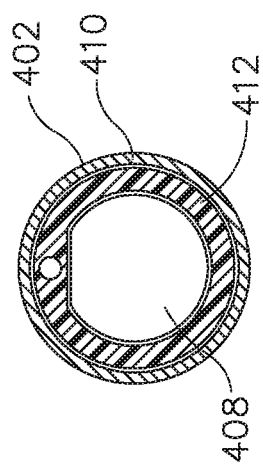
FIG. 13 depicts a cross-sectional view of the guide catheter of FIG. 12, with the cross-section taken along line 13-13 of FIG. 12.

FIG. 13 shows a cross-section of tubular shaft (402). As can be seen, shaft (402) has an outer shaft tube (410), an inner shaft tube (412). Outer shaft tube (410) and inner shaft tube (412) are substantially similar to shaft tubes (110, 112) described above such that shaft tubes (410, 412) will not be described in further detail. However, unlike shaft (102), shaft (402) comprises two lumens (408, 409) extending longitudinally through shaft (402). Lumens (408, 409) comprise a working lumen (408) and an access lumen (409). Working lumen (408) is generally configured such that balloon dilation catheter (200) may be slidably disposed within lumen (408) similar to lumen (108) described above. Access lumen (409) is configured to provide a passageway for wires and/or illuminating fibers, as will be described in greater detail below. Although the present example is equipped with a separate lumen (409) for wires and/or illuminating fibers, it should be understood that in other examples lumen (409) may be omitted and wires and/or illuminating fibers may extend through lumen (408). Alternatively, any wires and/or illuminating fibers used with guide catheter (400) may be directly overmolded or otherwise incorporated into shaft tubes (410, 412) or the interface between shaft tubes (410, 412). By way of example only, in some variations a set of conductive traces are interposed between shaft tubes (410, 412) and extend along the length of shaft (402).

Figure 14:
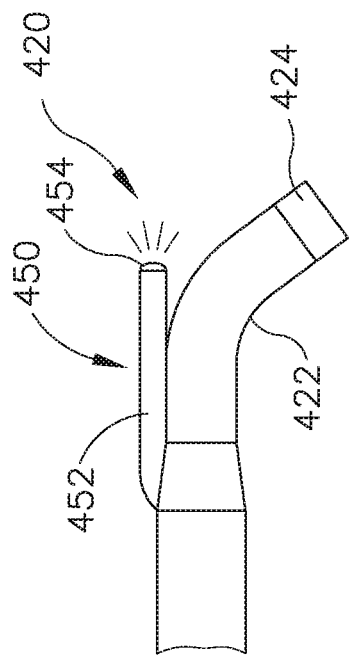
FIG. 14 depicts a detailed side view of the distal end of the guide catheter of FIG. 12.

FIG. 14 shows a detailed view of distal portion (420) of guide catheter (400). Distal portion (420) of the present example includes a bend (422) similar to bend (122) described above. Distal portion (420) of guide catheter (400) further includes a distal tip (424). Distal tip (424), like distal tip (124) described above, comprises a transparent material to permit dilation catheter (200) to be visible through distal tip (424). In addition to distal tip (424) being comprised of a transparent material, such a material may also be configured to be more flexible relative to the material of elongate shaft (402) such that distal tip (424) is atraumatic in character.

Unlike distal portion (120) of guide catheter (100), distal portion (420) of guide catheter (400) further includes a visualization assembly (450). As seen in FIGS. 12 and 13, visualization assembly (450) comprises a visualization shaft (452) and distal lens (454). Visualization shaft (452) extends longitudinally from shaft (402) along an axis that is generally parallel to, yet laterally offset from, the longitudinal axis of shaft (402). In other words, while bend (422) deflects distal portion (420) of shaft (402) away from the longitudinal axis of shaft (402), visualization shaft (452) continues unbent, separating from shaft (402) at bend (422). Lens (454) curves convexly from the distal end of visualization shaft (452) and is generally configured to collect light from an area distal of the distal end of visualization shaft (452). In some variations, lens (454) comprises a gradient-index (GRIN) lens.

Figure 15:
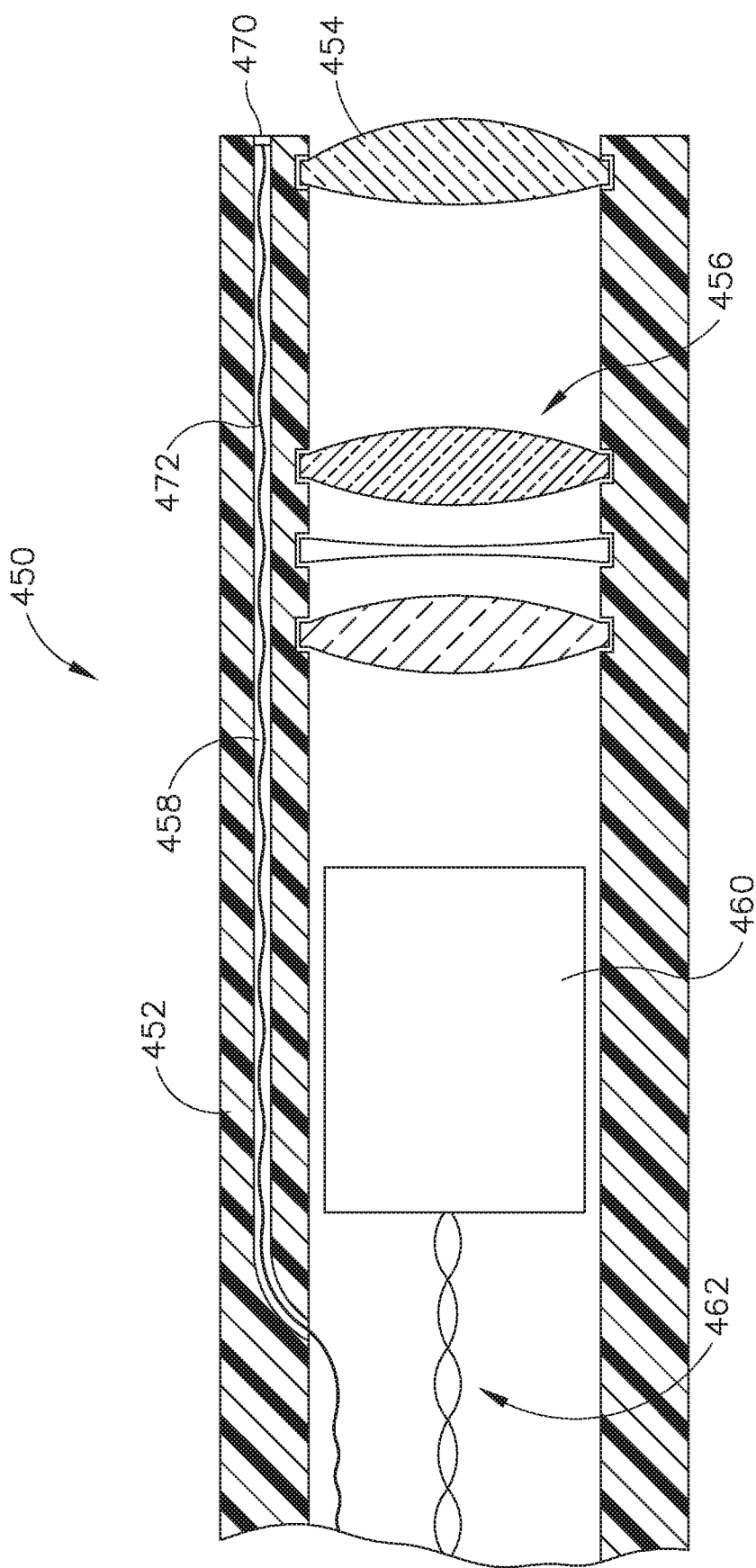
FIG. 15 depicts a cross-sectional side view of a visualization assembly of the guide catheter of FIG. 12.

FIG. 15 shows a detailed cross-section of visualization assembly (450). As can be seen, visualization shaft (452) houses distal lens (454), an objective lens assembly (456), and an image sensor (460). Additionally, visualization shaft (452) includes a light source (470) embedded in visualization shaft (452). As described above, distal lens (454) collects light from an area distal of distal lens (454). In some examples, distal lens (454) may have the characteristics of a wide angle lens such that distal lens (454) may permit visualization assembly (450) to visualize a large region surrounding distal lens (454) (i.e., a wide field of view). Of course, distal lens (454) may also comprise a lens having a any suitable focal length. Distal lens (454) further directs any collected light toward objective lens assembly (456). Objective lens assembly (456) is generally configured to focus light received from distal lens (454) and direct the light to image sensor (460). Additionally, objective lens assembly (456) may be configured to adjust certain properties (e.g., zoom, focal length, etc.) of the light as it travels through objective lens assembly (456). Although objective lens assembly (456) is shown as being comprised of three separate lens elements of a particular convexity or concavity, it should be understood that objective lens assembly (456) may comprise any suitable number of lenses having any suitable types of light receiving surface configurations (e.g., concavity, convexity). It should also be understood that objective lens assembly (456) may include one or more gradient-index (GRIN) lenses. In some examples objective lens assembly (456) may simply be omitted and distal lens (454) may direct light directly to image sensor (460). Various suitable components and configurations that may be used to form the optics of lens (454) and lens assembly (456) will be apparent to those of ordinary skill in the art in view of the teachings herein.

Image sensor (460) of the present example is shown schematically. Image sensor (460) may comprise any suitable conventional image sensor such as a micro-complementary metal-oxide semiconductor (CMOS) image sensor. One merely exemplary suitable sensor micro-CMOS image sensor may be the NanEye 1 mm×1 mm image sensor produced by AWAIBA Lba of Funchal, Madeira. Image sensor (460) is shown as being connected to a plurality of wires (462). Wires (462) extend proximally from image sensor (460) through shaft (402) via lumen (409) and out of the proximal end of shaft (402). Wires (462) permit image sensor (460) to receive power from a power source (not shown) and communicate image data to an image processing unit (not shown) which may include, or be connected to, a display (not shown). Although image sensor (460) is described herein as being separate from image processing components, it should be understood that in other examples image sensor (460) may include at least some image processing components onboard. In such examples, a separate image processing unit may be omitted and wires (462) may connect directly to a display.

Light source (470) of the present example comprises a light emitting diode secured within a lumen (458). Lumen (458) extends longitudinally through at least a portion of visualization shaft (452). At least one wire (472) extends proximally from light source (470) through lumen (458) and lumen (409) to provide electrical power to light source (470). Although not shown, wire (472) may eventually connect with wires (462) to permit wires (462, 472) to connect to the image processing unit using a single connector. In some examples, wire (472) may be omitted and an illumination fiber may be provided instead. In such examples, light source (470) may simply comprise a lens or transparent piece of plastic that is configured to transmit light travelling through the illumination fiber. In other examples, wire (472) may be omitted and lumen (458) may comprise a light pipe that is configured to transmit light to an optically transmissive element forming light source (470). Still other suitable ways of supplying light to the distal end of visualization assembly (450) will be apparent to those of ordinary skill in the art in view of the teachings herein.

Returning to FIG. 12, proximal portion (430) of guide catheter (400) is generally configured to aid in manipulating guide catheter (400) and to aid in inserting dilation catheter (200) into a Eustachian tube (26) using a single hand. Proximal portion (430) includes a proximal hub (432), a proximal end (434), and a middle section (436), Proximal hub (432) is configured to aid in insertion of dilation catheter (200) into Eustachian tube (26). Proximal end (434) and middle section (436) are configured to facilitate stabilization of guide catheter (400) when guide catheter (400) is inserted into a nose.

B. Exemplary Use of Catheter with Integral Camera

Figure 16A:
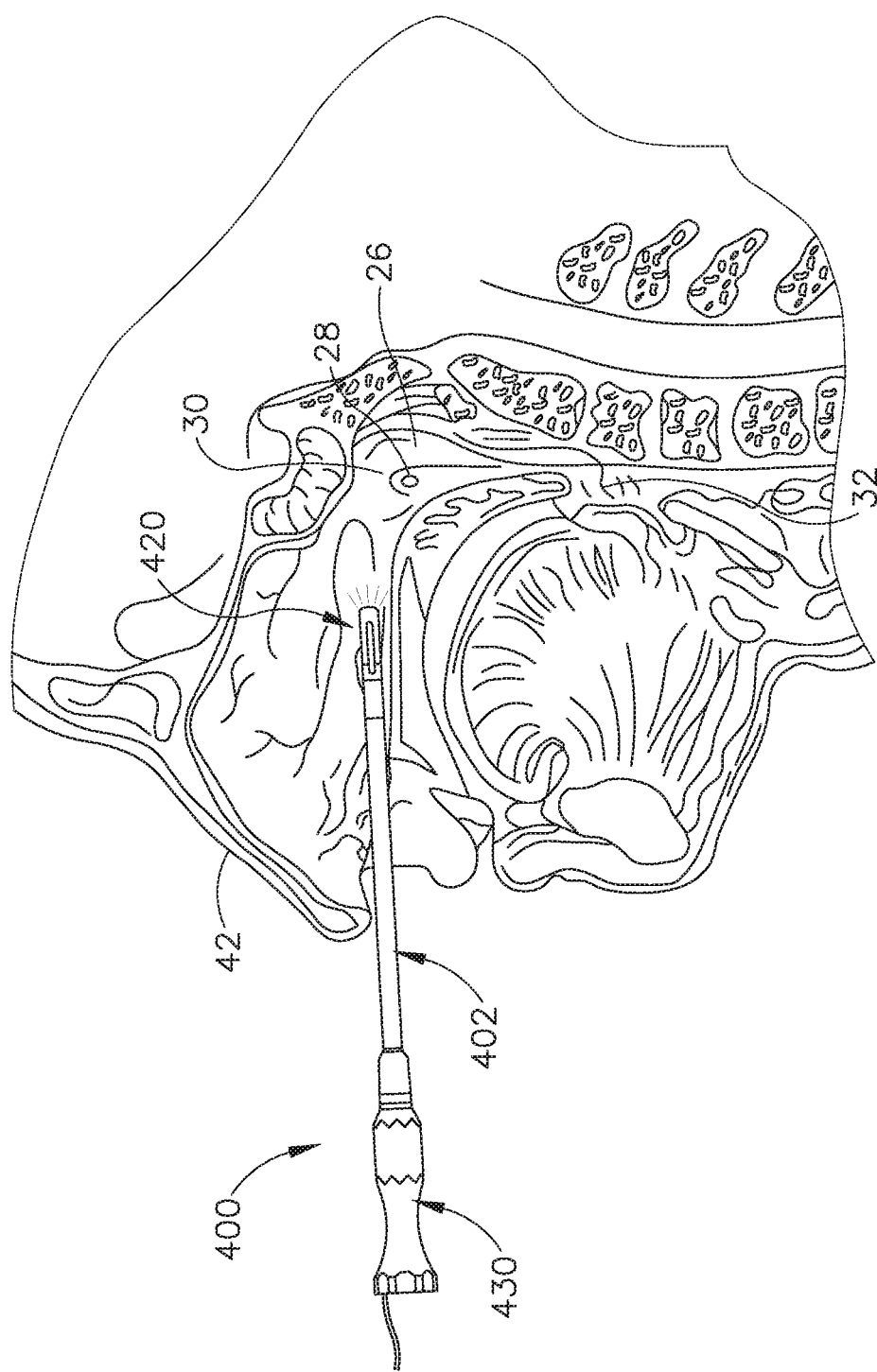
FIG. 16A depicts a cross-sectional view of the head of FIG. 2, with the guide catheter of FIG. 12 inserted into the nasal cavity.

An exemplary use of guide catheter (400) in conjunction with dilation catheter (200) is shown in FIGS. 16A-17C. As can be seen in FIG. 16A, an operator may initially insert guide catheter (400) into the patient's nose (42) via a nostril. Guide catheter (400) may be advanced through the patient's nasal cavity toward the ostium (28) of the Eustachian tube (26). As guide catheter (400) is advanced, the operator may simultaneously rotate guide catheter (400) such that bend (422) orients distal end (406) of shaft (402) toward Eustachian tube (26). Because visualization assembly (450) provides a line of sight that is parallel to the longitudinal axis of shaft (402), visualization assembly (450) visualizes the area of the patient's nasal cavity immediately ahead of guide catheter (400). Such a view may provide an operator with an enhanced ability to advance guide catheter (400) towards ostium (28) of Eustachian tube (26).

Figure 16B:
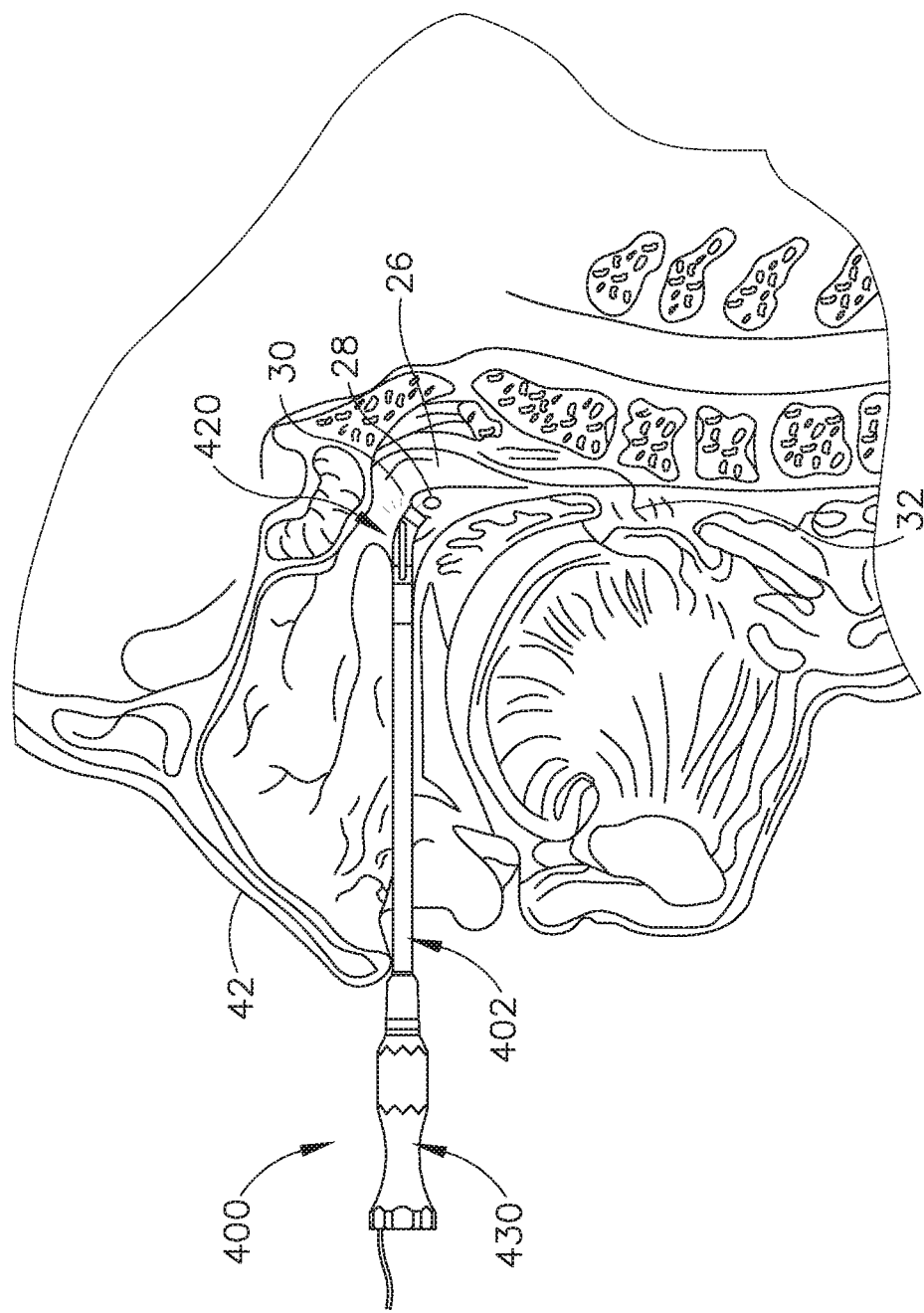
FIG. 16B depicts a cross-sectional view of the head of FIG. 2, with the guide catheter of FIG. 12 advanced to a position in the nasopharynx adjacent to an ostium of the Eustachian tube.
Figure 16C:
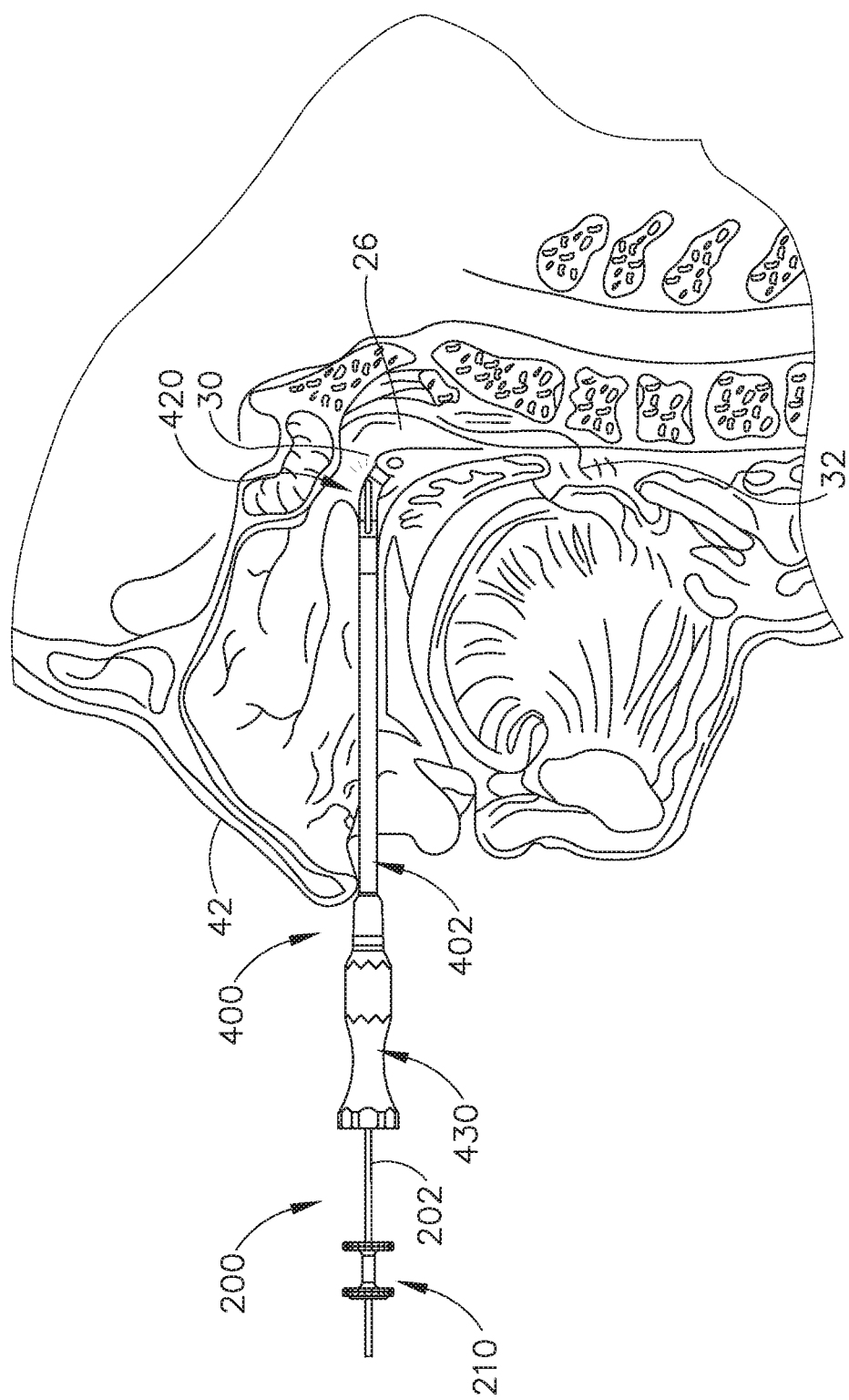
FIG. 16C depicts a cross-sectional view of the head of FIG. 2, with the dilation catheter of FIG. 9A inserted into the guide catheter of FIG. 12.
Figure 17A:
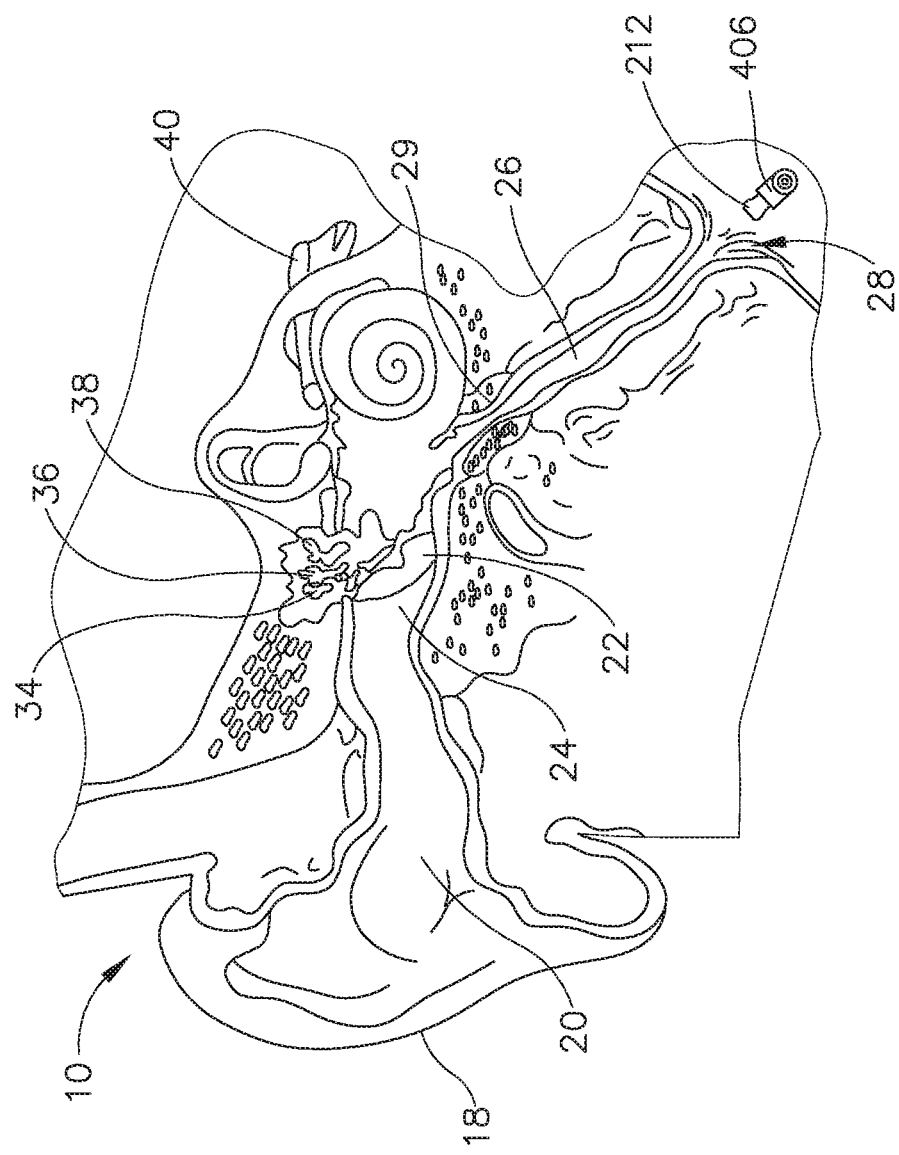
FIG. 17A depicts a cross-sectional view of the ear of FIG. 1, with the guide catheter of FIG. 12 and the dilation catheter of FIG. 9A positioned adjacent to the Eustachian tube.

Under the guidance of visualization assembly (450) of guide catheter (400), guide catheter (400) is positioned such that distal end (406) of guide catheter (400) is approximately adjacent to ostium (28) of Eustachian tube (26), as seen in FIG. 16B. With distal end (406) of guide catheter (400) positioned at a location approximately adjacent to ostium (28) an operator may begin advancing dilation catheter (200) relative to guide catheter (400). As can best be seen in FIG. 16C, dilatation catheter (200) is inserted through proximal end (404) of guide catheter (400) and through lumen (408) toward distal end (406) of guide catheter (400). As best seen in FIG. 17A, tip (212) of dilation catheter (200) will eventually exit distal end (406) of guide catheter (400) and thereby move toward the ostium (28) of the Eustachian tube (26). In some variations, dilation catheter (200) is pre-inserted in guide catheter (400) at the beginning of the process, such that dilation catheter (200) is already disposed in guide catheter (400) during the stages shown in FIGS. 16A and 16B, with tip (212) of dilation catheter (200) being substantially flush with distal end (406) of guide catheter (400).

Figure 16D:
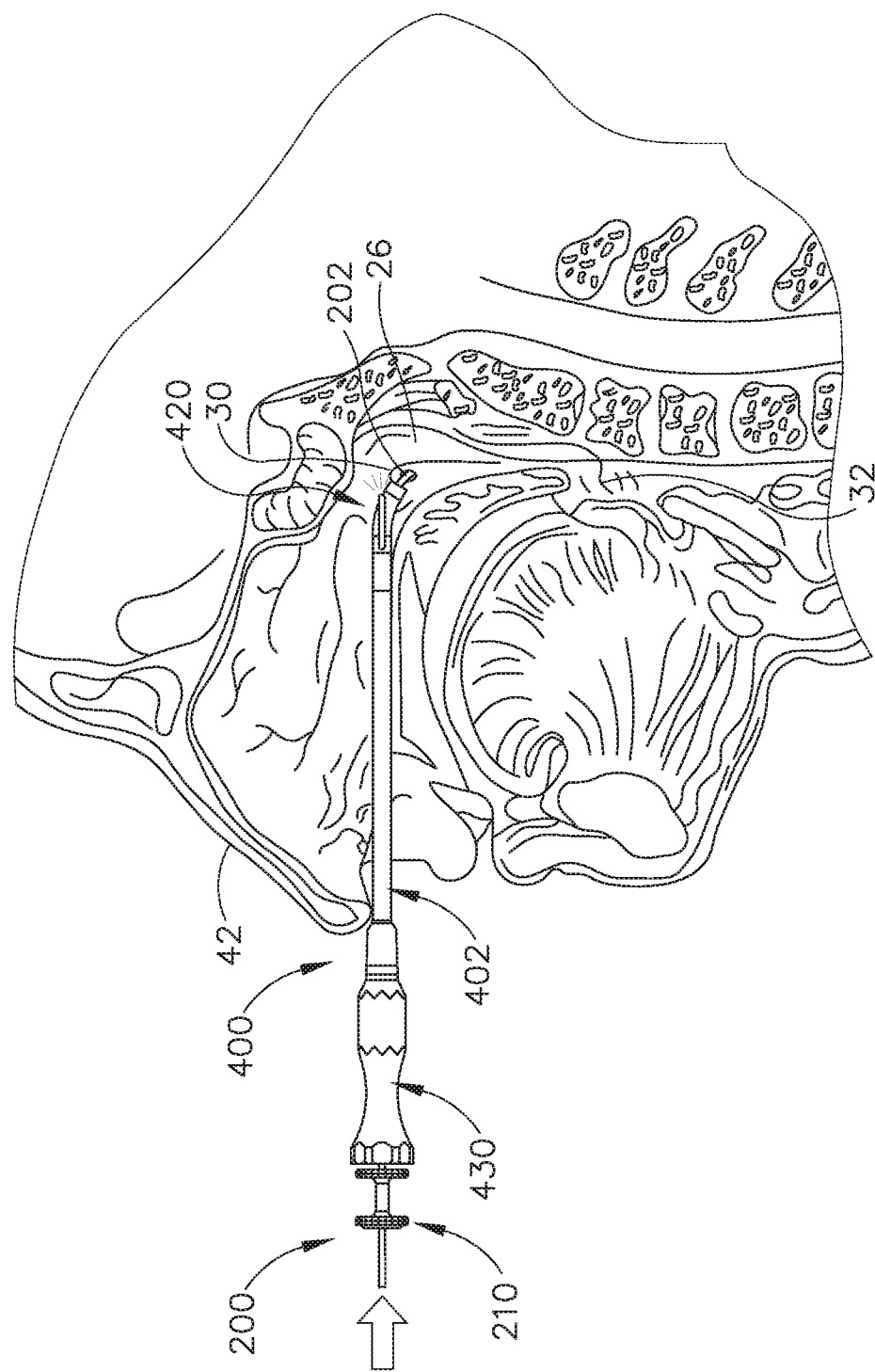
FIG. 16D depicts a cross-sectional view of the head of FIG. 2, with the dilation catheter of FIG. 9A advanced distally through the guide catheter of FIG. 12 and into the Eustachian tube.
Figure 17B:
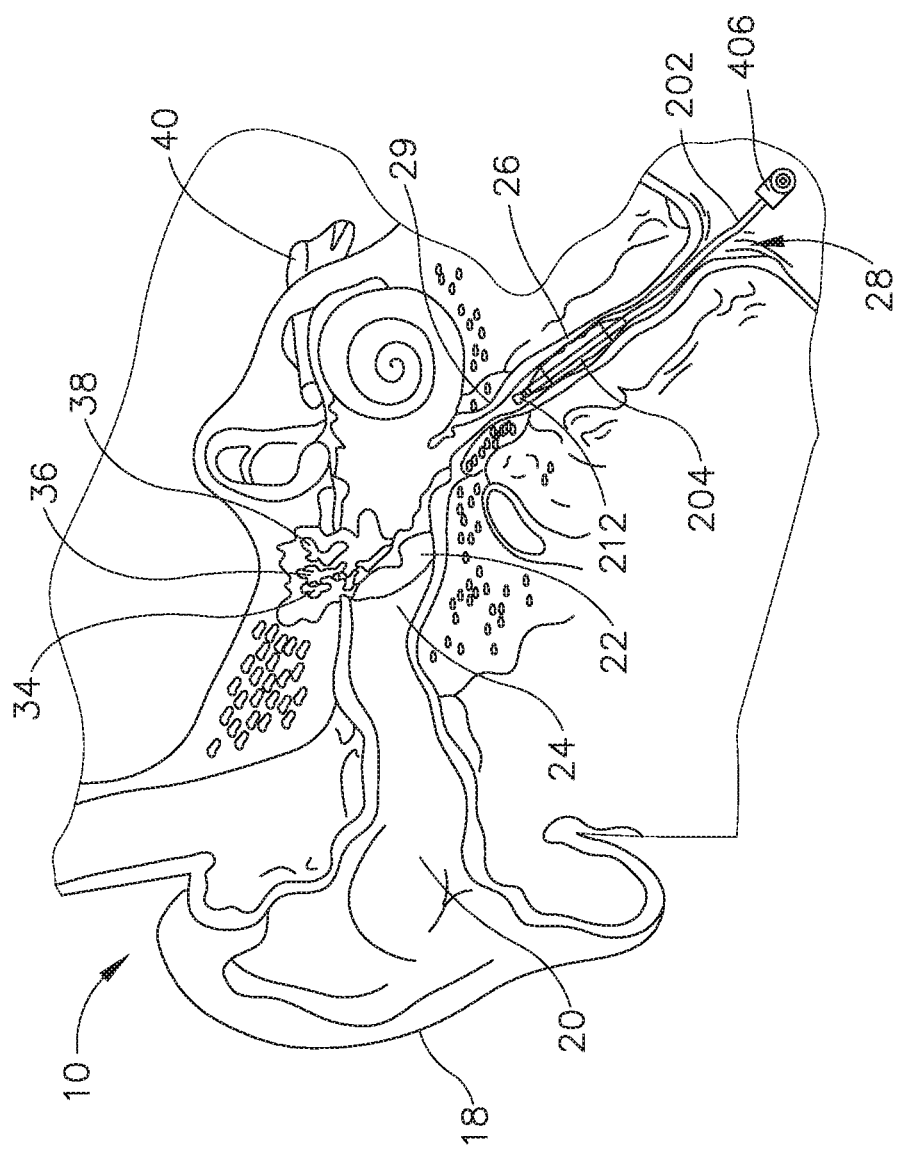
FIG. 17B depicts a cross-sectional view of the ear of FIG. 1, with the dilation catheter of FIG. 9A advanced into the Eustachian tube.
Figure 17C:
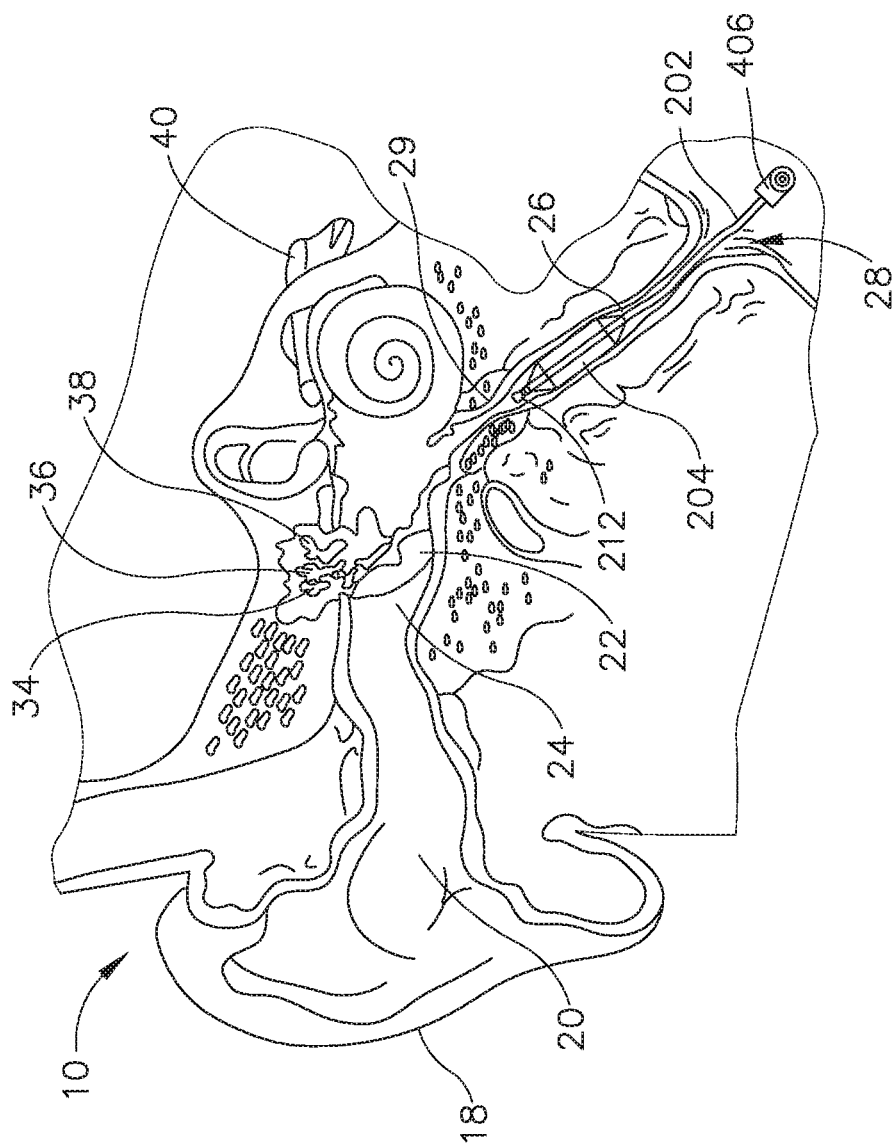
FIG. 17C depicts a cross-sectional view of the ear of FIG. 11, with a balloon of the dilation catheter of FIG. 9A expanded to an inflated state within the Eustachian tube.

Once the operator has achieved a desired initial positioning of dilation catheter (200), the operator may begin advancement of dilation catheter (200) into Eustachian tube (26). In particular, as can be seen in FIGS. 16D and 17B, the operator may grasp actuator (210) of dilation catheter (200) while holding guide catheter (400) steady and advance dilation catheter (200) relative to guide catheter (400). Distal end (218) of dilation catheter (200) is then advanced into Eustachian tube (26). The operator may continue advancing dilation catheter (200) until balloon (20.4) reaches a desired location within Eustachian tube (26). Once balloon (204) reaches the desired location, the operator may initiate dilation by expanding balloon (204). FIG. 17C shows balloon (204) in the expanded configuration. The operator may maintain balloon (204) in the expanded configuration for any suitable period of time sufficient to complete dilation as similarly described above with respect to balloon catheter (200). The operator may also repeatedly inflate and deflate balloon (204) any suitable number of times. Once the dilation procedure is complete, the operator may retract balloon catheter (200) and guide catheter (400), leaving Eustachian tube (26) dilated.

It should be understood that although guide catheter (400) and dilation catheter (200) are described herein as being used together, in other alternative uses guide catheter (400) or dilation catheter (200) may be readily substituted for other instruments described herein as will be apparent to those of ordinary skill in the art. For instance, guide catheter (400) may be used with dilation catheter (200); or guide catheter (100) may be used with dilation catheter (200). Moreover, although dilation catheter (200) is described herein as being used to merely dilate Eustachian tube (26), it should be understood that in other examples dilation catheter (200) may also be used to inject fluids and/or therapeutic substances into Eustachian tube (26), deposit a stent carried by dilation catheter (200) into Eustachian tube (26), and/or for various other purposes.

In some instances, lens (454) or image sensor (260) (or some optically transmissive feature that is distal to image sensor (260) as described above) may become covered with mucus and/or other debris making it difficult to obtain satisfactory images from image sensors (460). It may therefore be desirable to include one or more features that are operable to clean away such debris. By way of example only, guide catheter (400) and/or dilation catheter (200) may include a wiping feature that is configured and operable in accordance with at least some of the teachings of U.S. Pub. No. 2014/0261545, entitled "Apparatus for Wiping Angled Window of Endoscope," published Sep. 18, 2014, now abandoned, the disclosure of which is incorporated by reference herein. As another merely illustrative example, guide catheter (400) and/or dilation catheter (200) may include a flushing feature that is operable to flush debris away using a cascade of fluid in accordance with at least some of the teachings of U.S. Pub. No. 2014/0261579, entitled "Apparatus for Flushing Angled Window of Endoscope," published Sep. 18, 2014, now abandoned, the disclosure of which is incorporated by reference herein. Other suitable features that may be used to provide cleaning of lens (454) or image sensor (260) (or some optically transmissive feature that is distal to image sensor (260) as described above) will be apparent to those of ordinary skill in the art in view of the teachings herein.

While guide catheter (400) and dilation catheter (200) are described above as being used to dilate the Eustachian tube (26), it should be understood that guide catheter (400) and dilation catheter (200) may be readily modified or otherwise used to provide dilation associated with paranasal sinuses. By way of example only, guide catheter (400) and dilation catheter (200) may be used to dilate a maxillary sinus ostium, a sphenoid sinus ostium, one or more openings associated with one or more ethmoid sinus air cells, the frontal recess, and/or other passageways associated with paranasal sinuses. Various suitable ways in which guide catheter (400) and/or dilation catheter (200) may be modified or otherwise used to dilate a maxillary sinus ostium, a sphenoid sinus ostium, one or more openings associated with one or more ethmoid sinus air cells, the frontal recess, and/or other passageways associated with paranasal sinuses will be apparent to those of ordinary skill in the art in view of the teachings herein.

IV. Exemplary Alternative Instruments for Eustachian Tube Treatment Procedures

Figure 18:
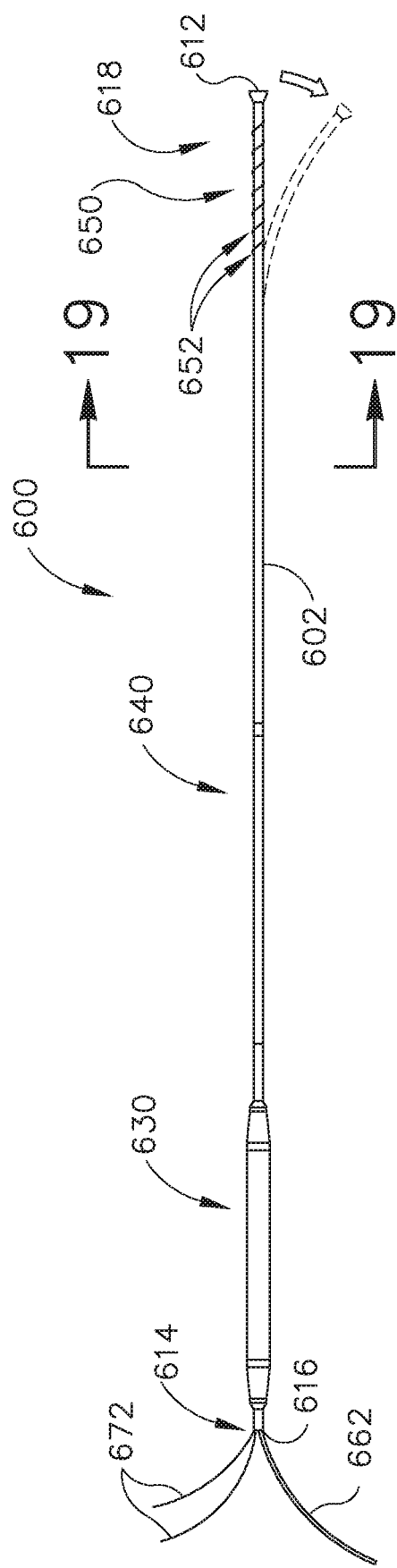
FIG. 18 depicts a side elevational view of an exemplary alternative catheter for use in treating a Eustachian tube.
Figure 20:
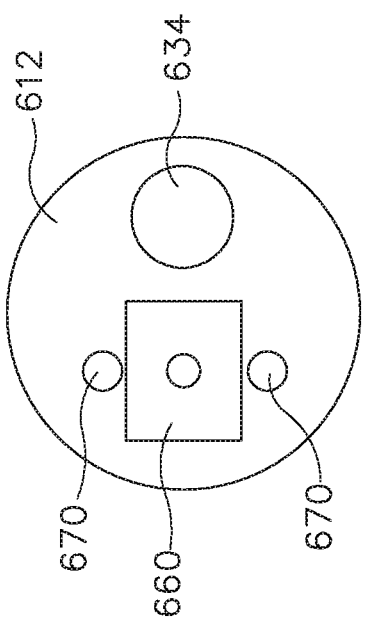
FIG. 20 depicts a front plan view of the distal end of the catheter of FIG. 18.
Figure 19:
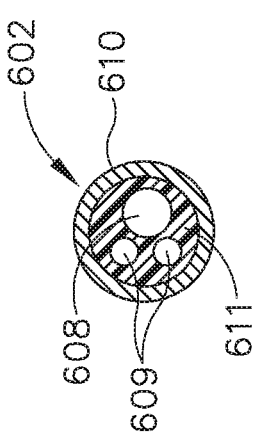
FIG. 19 depicts a cross-sectional view of a shaft of the catheter of FIG. 18, with the cross-section taken along line 19-19 of FIG. 18.

FIGS. 18-20 show an exemplary alternative cannula (600) for use in procedures for treatment of a Eustachian tube (26). Cannula (600) incorporates at least some of the features of guide catheters (100, 400) and dilation catheter (200) described above. As can be seen in FIG. 18, cannula (600) comprises an elongate shaft (602) having a distal end (618) and a proximal end (614). As will be described in greater detail, distal end (618) generally comprises a distal flexible portion (650) and a blunt distal tip (612). As will also be described in greater detail below, proximal end (614) generally comprises a proximal grip (630) and a proximal opening (616).

Shaft (602) extends through the entire length of cannula (600). Shaft (602) further includes a rigid proximal portion (640) that extends between proximal grip (630) and distal flexible portion (650). As can best be seen in FIG. 19, shaft (602) is constructed of two layers of material. For instance, shaft (602) includes an outer tube (610) that may be comprised of a rigid biocompatible material such as stainless steel. By way of example only, outer tube (610) may comprise a hypotube having a length of approximately 11 inches, an outer diameter of approximately 0.085 inches, and an inner diameter of approximately 0.064 inches. Alternatively, any other suitable dimensions may be used. Shaft (602) further includes an inner core (611). Inner core (611) is flexible relative to outer tube (610) and may comprise any suitable material such as polyimide or any other suitable polymer. As will be described in greater detail below, inner core (611) may provide flexibility to shaft (602) through distal flexible portion (650). By way of example only, inner core may have an outer diameter of approximately 0.023 inches and an inner diameter of approximately 0.020 inches. Alternatively, any other suitable dimensions may be used.

Inner core (611) defines a plurality of lumens extending longitudinally through shaft (602) from distal end (618) to proximal end (614). As can be seen, inner core (611) includes a working lumen (608) and two access lumens (609). Working lumen (608) is configured to receive various working instruments. By way of example only, in some examples working lumen (608) may receive a laser fiber, which may be used to perform a treatment procedure on a Eustachian tube (26). As will be described in greater detail below, access lumens (609) may receive wires and/or illumination fibers to connect an image sensor (660) and at least one light source (670) to an image processing unit, display, and/or light source.

Returning to FIG. 18, proximal grip (630) of proximal end (614) is generally configured for gripping of cannula (600) by an operator. Proximal grip (630) is disposed adjacent to proximal opening (616) and comprises a rounded cross-section that increases the diameter of shaft (602) to improve an operator's grip of cannula (600). Thus, cannula (600) may be readily manipulated by an operator gripping proximal grip (630).

Proximal opening (616) is open to lumens (608, 609) of shaft (602), thereby permitting proximal communication with lumens (608, 609) through proximal opening (616). Accordingly, proximal opening (616) may provide an exit point from cannula (600) for wires and/or illuminating fibers as will be described in further detail below. Proximal opening (616) further provides an access point suitable for any working instrument to be inserted into working lumen (608), as will also be further described below.

As noted above, distal portion (618) includes distal flexible portion (650) and blunt distal tip (612). Flexible portion (650) is generally flexible such that at least a portion of shaft (602) may be flexed as shown in phantom in FIG. 18. To permit flexibility of distal flexible portion (650), outer tube (610) of shaft (602) includes a spiral cut (652) that comprises a cut transversely through outer tube (610) extending in a spiral pattern longitudinally though the length of distal flexible portion (650). Spiral cut (652) permits outer tube (610) to laterally deflect from the longitudinal axis of shaft (602), thereby permitting outer tube (610) to flex. It should be understood that spiral cut (652) is only through outer tube (610) such that inner core (611) remains fully intact. Thus, the particular amount of flexibility of distal flexible portion (650) is determined at least in part by the particular material used for inner core (611). The flexibility may also be influenced by the helix angle of spiral cut (652). In the present example, spiral cut (652) extends along approximately 5.5 cm of the length of outer tube (610), though it should be understood that spiral cut (652) may extend along any other suitable length.

Tip (612) is similar to tip (212) described above. In particular, tip (612) includes an image sensor (660) and a plurality of light sources (670). As can best be seen in FIG. 20, image sensor (660) is positioned adjacent to working lumen (608), which extends through tip (612). In the present example, image sensor (660) is mounted to tip (612) via a flexible bonding adhesive, such as Ultra Light-Weld™ flexible catheter bonding adhesive, to enhance the atraumatic nature of tip (612). Of course, in other examples image sensor 66 may be secured to tip (612) using any other suitable means.

Image sensor (660) is similar to image sensor (260) described above with respect to dilation catheter (200). Like image sensor (260), image sensor (660) of this example may optionally be equipped with one or more lens elements and/or other optically transmissive features that are positioned distal to image sensor (660) to enhance imaging through image sensor (660) and/or to protect image sensor (660). Image sensor (660) connects to a wire bundle (662), which is threaded through one or more of access lumens (609) and out of proximal opening (616). Like with image sensor (460) described above, image sensor (660) may connect with an image processor (not shown) via wire bundle (662).

Light sources (670) are generally configured to project light distally from tip (612) to illuminate a visualization area that is disposed distally of tip (612). Light sources (670) of the present example include two lenses disposed within tip (212) connected to two corresponding illumination fibers (672). However, it should be understood that light sources (670) may comprise any suitable light emitting feature such as a light emitting diode or a lens connected to a light tube formed in shaft (602). Light sources (670) may be configured to provide illumination in the visual light spectrum, infrared spectrum, or some other selected bandwidth. It should also be understood that tip (612) may include just one light source (670) instead of two light sources (670). In versions where light sources (670) comprise an optical fiber, such an optical fiber may have an outer diameter of approximately 0.009 inches or any other suitable outer diameter.

In an exemplary use of cannula (600), an operator may insert cannula (600) into the patient's nose (42) via a nostril. The operator may guide cannula (600) the ostium (28) of the Eustachian tube (26) under visualization provided through image sensor (660). Proximal grip (630) may be gripped by an operator to manipulate cannula (600) as it is advanced through the patient's nasal cavity. Once cannula (600) is advanced to a position adjacent to the ostium (28) of the Eustachian tube (26), the operator may further manipulate cannula (600) under the visual guidance from image sensor (660) to advance distal end (618) into the Eustachian tube (26). Once distal end (618) is positioned within the Eustachian tube (26), cannula (600) may be further advanced as desired until the operator identifies a region of the Eustachian tube (26) for treatment. Once a treatment region is identified, the operator may thread a working instrument such as a laser fiber through working lumen (608) and out through distal tip (612) to a position adjacent to the treatment region. A treatment procedure may be performed and then the operator may remove cannula (600).

Figure 21:
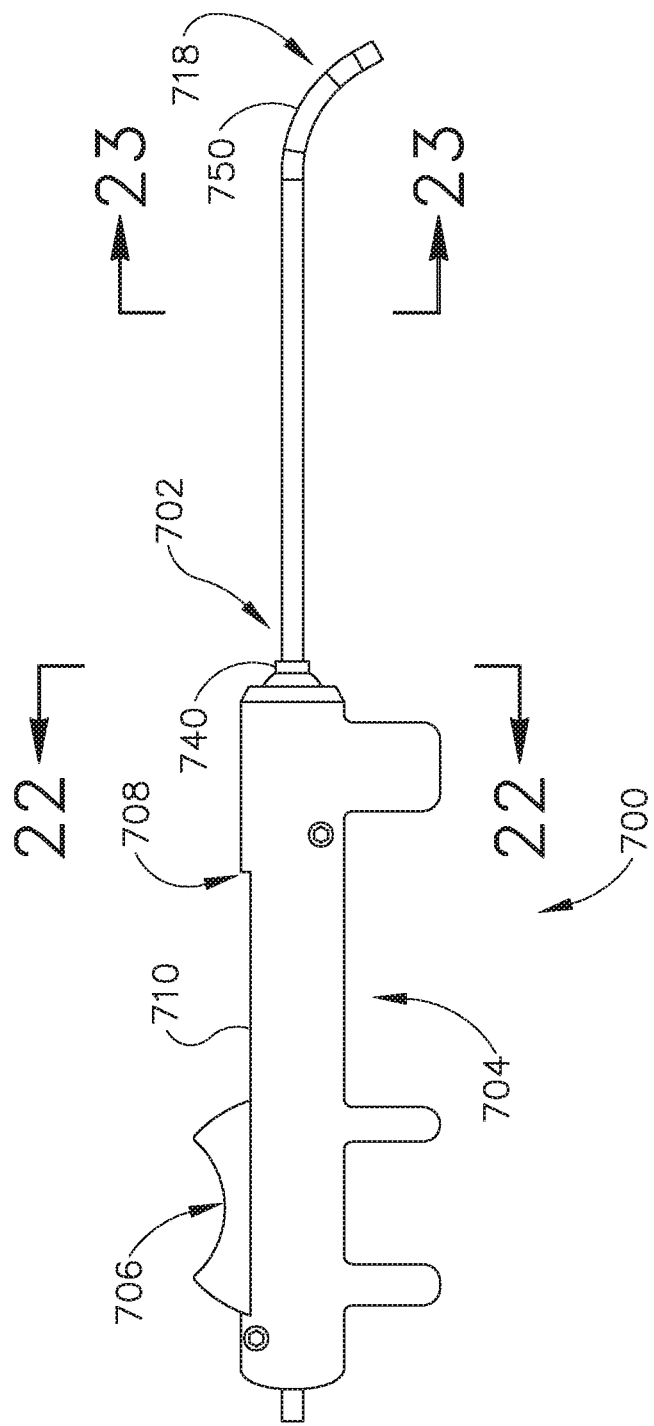
FIG. 21 depicts a side elevational view of still another exemplary alternative guide catheter.
Figure 23:
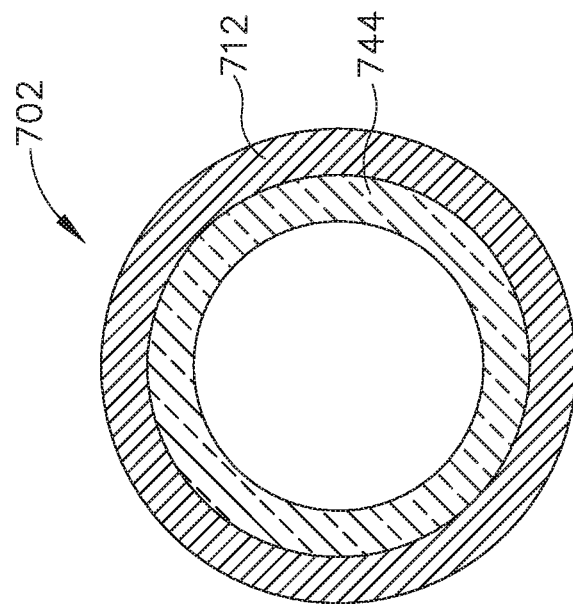
FIG. 23 depicts a cross-sectional view of a shaft of the guide catheter of FIG. 21, with the cross-section taken along line 23-23 of FIG. 21.
Figure 22:
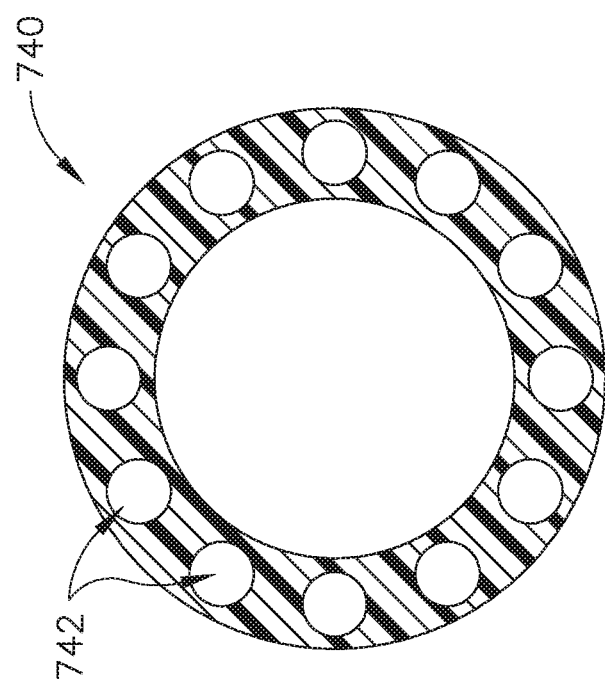
FIG. 22 depicts a cross-sectional view of the guide catheter of FIG. 21, with the cross-section taken along line 22-22 of FIG. 21.

FIGS. 21-23 show an exemplary alternative guide catheter (700) that is substantially the same as guide catheter (300) described above, except as where otherwise noted herein. As can be seen in FIG. 21, guide catheter (700) of the present example comprises an elongate shaft (702), which is substantially the same as shaft (302) described above. Guide catheter (700) further comprises a handle (704), which is substantially the same as handle (304) described above. In particular, handle (704) comprises an actuator (706) that may be attached to dilation catheter (200) such that actuator (206) may be used to advance dilation catheter (200) relative to guide catheter (700). As can be seen, handle (704) includes an elongate track (710), which slidably supports actuator (706), thereby permitting actuator (706) to slide longitudinally relative to handle (704). Track (710) further includes a stop (708), which may prevent over insertion of dilation catheter (200) into a Eustachian tube (26).

Unlike guide catheter (300), guide catheter (700) includes an illuminated bend window (750) positioned adjacent to (yet proximal to) a distal end (718) of shaft (702). In particular, bend window (750) comprises a generally transparent window that may permit an operator to view dilation catheter (200) through shaft (702) as dilation catheter (200) is advanced through guide catheter (700). In the present example, bend window (750) comprises a high clarity transparent light conducting polymer, although any other suitable transparent material may be used. Additionally, it should be understood that bend window (750) of the present example is transparent for 360 degrees around shaft (702). In other examples, bend window (750) may comprise materials with differing optical transmissivity to provide variable transparency. For instance, in some variations one 180 degree section of bend window (750) may be comprised of a relatively opaque material, while the other 180 section of bend window (750) may comprise the transparent material described above. In such an example, only a portion of bend window (750) may permit an operator to view dilation catheter (200) through shaft (702).

To assist in viewing of dilation catheter (200) through bend window (750), bend window (750) is illuminated. In particular, adjacent to the distal end of handle (704), shaft (702) includes an illuminating array (740). Illuminating array (740) is shown in cross-section in FIG. 22. As can be seen, illuminating array (740) includes a plurality of light emitters (742) disposed circumferentially around illuminating array (740). Light emitters (742) comprise a plurality of illuminating fibers terminating at illuminating array (740). Light emitters (742) may further include lenses or other features that may be configured to direct light. Of course, in other examples light emitters (742) may include any other suitable light emitting feature such as light emitting diodes, a single light tube, and/or any other light emitting feature as will be apparent to those of ordinary skill in the art in view of the teachings herein.

As can be seen in FIG. 23, shaft (702) comprises an exterior tube (712) and an interior light communicating portion (744). Exterior tube (712) comprises a generally rigid material such as metal. Interior light communicating portion (744) is in communication with illuminating array (740) and is generally configured to transfer light from illuminating array (740) through shaft (702) to bend window (750). Interior light communicating portion (7.44) of the present example comprises a high clarity light conducting polymer, although any suitable light conducting material may be used. Thus, interior light communicating portion (744) may act as a light pipe. In some examples interior light communicating portion (744) and bend window (750) may comprises a single unitary part. However, no such limitation is intended and in other examples interior light communicating portion (744) and bend window (750) may simply comprise separate components. It should also be understood that some versions of shaft (702) may include a plurality of optical fibers running from illuminating array (740) to bend window (750), such that the optical fibers convey the light along the length of shaft (702) instead of having an interior light communicating portion (744) convey the light.

In an exemplary use of guide catheter (700), guide catheter (700) is gripped by an operator using a handle (704) and shaft (702) is inserted into a nostril of a patient. Because actuator (706) of guide catheter (700) may be attached to dilation catheter (200), it should be understood that as guide catheter (700) is inserted into the nostril, dilation catheter (200) may likewise be inserted into the nostril. However, dilation catheter (200) may remain within shaft (702) until an operator desires to advance dilation catheter (200).

Guide catheter (700) may be advanced within a nostril of the patient until the distal end of shaft (202) is adjacent to the ostium (28) of the Eustachian tube (26). At such a point, the operator may begin advancing dilation catheter (200) separately from guide catheter (300). To provide such advancement, the operator may slide actuator (706) along track (710). As dilation catheter (200) is advanced through shaft (702), an operator may view the advancement of dilation catheter (200) through bend window (750). Visualization of dilation catheter (200) may assist operator in identifying certain depth indicating markers on the surface of dilation catheter (200), thereby providing the operator with enhanced visual feedback indicating the depth of advancement of dilation catheter (200) relative to guide catheter (700). By way of example only, the operator may view bend window (750) using an Acclarent Cyclops™ Multi-Angle Endoscope by Acclarent, Inc. of Menlo Park, Calif. and/or an endoscope that is configured and operable in accordance with the teachings of U.S. Pub. No. 2010/0030031, entitled "Swing Prism Endoscope," published Feb. 4, 2010, now abandoned, the disclosure of which is incorporated by reference herein.

Actuator (706) may be advanced until either dilation catheter (200) is advanced to a desired position or until actuator (706) reaches stop (708). Regardless, once dilation catheter (200) is positioned at a desired position in the Eustachian tube (26), the operator may expand balloon (204) of dilation catheter (200) to dilate the Eustachian tube (26) similarly as described above. It should be understood that, in addition to promoting visualization of depth indicating markers on the surface of dilation catheter (200), the illuminated bend window (750) may also convey light into the nasal cavity, thereby facilitating visualization of the ostium (28) of the Eustachian tube (26).

While cannula (600) and guide catheter (700) are described above as being used with respect to the Eustachian tube (26), it should be understood that cannula (600) and guide catheter (700) may also be used in procedures involving the paranasal sinuses. By way of example only, guide cannula (600) or guide catheter (700) may be used in procedures to dilate a maxillary sinus ostium, a sphenoid sinus ostium, one or more openings associated with one or more ethmoid sinus air cells, the frontal recess, and/or other passageways associated with paranasal sinuses. Various suitable ways in which cannula (600) and/or guide catheter (700) may be modified or otherwise used to dilate a maxillary sinus ostium, a sphenoid sinus ostium, one or more openings associated with one or more ethmoid sinus air cells, the frontal recess, and/or other passageways associated with paranasal sinuses will be apparent to those of ordinary skill in the art in view of the teachings herein.

V. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A dilation catheter system, wherein the dilation catheter system comprises: (a) a guide member, wherein the guide member includes a shaft comprising a distal end and a proximal end, wherein the shaft defines a longitudinal axis; (b) a dilation catheter movable relative to the guide member, wherein the dilation catheter comprises an expandable dilator, wherein the expandable dilator is sized to fit within one or both of a Eustachian tube or a passageway associated with a paranasal sinus; and (c) an image sensor, wherein the image sensor is configured to provide visualization within anatomy of a patient, wherein the image sensor is integral with the guide member.

Example 2

The dilation catheter system of Example 1, wherein the image sensor is located at the distal end of the guide member.

Example 3

The dilation catheter system of any one or more of Examples 1 through 2, wherein the guide member further comprises a visualization assembly, wherein the image sensor is integrated into the visualization assembly, wherein at least a portion of the visualization assembly projects outwardly from the distal end of the guide member along an axis parallel to the longitudinal axis of the shaft of the guide member.

Example 4

The dilation catheter system of Example 3, wherein the visualization assembly further comprises an illumination feature.

Example 5

The dilation catheter system of Example 4, wherein the illumination feature comprises a light emitting diode.

Example 6

The dilation catheter system of any one or more of Examples 4 through 5, wherein the illumination feature comprises an optical fiber.

Example 7

The dilation catheter system of any one or more of Examples 4 through 6, wherein the illumination feature is laterally offset from the longitudinal axis of the shaft of the guide member.

Example 8

The dilation catheter system of any one or more of Examples 3 through 7, wherein the visualization assembly further comprises an objective lens positioned distal to the image sensor.

Example 9

The dilation catheter system of any one or more of Examples 3 through 8, wherein the distal end of the guide member includes a bent region, wherein the bent region curves away from the visualization assembly.

Example 10

The dilation catheter system of any one or more of Examples 1 through 9, wherein the guide member comprises a guide catheter.

Example 11

The dilation catheter system of any one or more of Examples 1 through 10, wherein the guide member is rigid, wherein the dilation catheter further comprises a flexible portion, wherein the flexible portion is flexible relative to the rigid guide member.

Example 12

The dilation catheter system of any one or more of Examples 1 through 11, wherein the guide member includes a bent portion, wherein the bent portion is configured to direct the dilation catheter into a Eustachian tube when the dilation catheter is moved relative to the guide member.

Example 13

The dilation catheter system of any one or more of Examples 1 through 12, wherein the dilation catheter comprises: (i) a first region, wherein the proximal region has a first diameter, (ii) a second region, wherein the second region has a second diameter, wherein the first diameter is smaller than the second diameter, wherein the second diameter is configured to prevent the dilation catheter from advancing into an isthmus of an Eustachian tube, and (iii) at least one lumen, wherein at least one lumen extends through the first region and through the second region.

Example 14

The dilation catheter system of any one or more of Examples 1 through 13, wherein the dilator of the dilation catheter has a bulbous distal tip.

Example 15

The dilation catheter system of any one or more of Examples 1 through 14, wherein the guide member further includes a lumen extending longitudinally through the shaft, wherein the lumen is configured to slidably receive the dilation catheter therein.

Example 16

A guide assembly, comprising: (a) an elongate shaft, the elongate shaft comprising: (i) a proximal portion, wherein the proximal portion is rigid, (ii) a distal portion, wherein the distal portion is curved or bendable, wherein the distal portion is configured to fit in a nasal cavity, and (iii) a lumen extending from the proximal portion to the distal portion, wherein the lumen is configured to slidably receive a working instrument; (b) a grasping feature positioned at the proximal portion of the elongate shaft; and (c) an imaging assembly integrated with the distal portion of the elongate shaft, wherein the imaging assembly comprises: (i) an image sensor, and (ii) a light feature configured to provide illumination.

Example 17

The guide assembly of Example 16, wherein the shaft comprises a hypotube, wherein the distal portion has a spiral cut configured to provide bendability to the hypotube.

Example 18

The guide assembly of Example 17, wherein the shaft further comprises a polymeric core member positioned within the hypotube, wherein the lumen is defined in the polymeric core member.

Example 19

A guide assembly, comprising: (a) an elongate shaft configured to cooperate with a working device, the elongate shaft comprising: (i) a proximal region, wherein the proximal region is rigid, and (ii) a distal region, wherein the distal region includes a bent portion, wherein the bent portion includes an optically transmissive window; (b) a grasping feature positioned at the proximal portion of the elongate shaft; and (c) an illuminating feature, wherein the illuminating feature is configured to provide light to the optically transmissive window of the shaft.

Example 20

The guide assembly of Example 19, wherein the illuminating feature comprises: (i) at least one light source located in the grasping feature, and (ii) at least one optical fiber or light pipe extending from the light source to the optically transmissive window.

VI. Miscellaneous

In some variations, dilation catheter (200) includes an integral image sensor and/or illuminating feature. By way of example only, dilation catheter (200) may be constructed and operable in accordance with at least some of the teachings of U.S. Provisional Patent App. No. 62/139,933, entitled "Balloon Catheter with Image Capture and Light Emission Features," filed Mar. 30, 2015, the disclosure of which is incorporated by reference herein. In versions where guide catheter (400, 600) and a dilation catheter (200) with an integral image sensor are used together, the optics associated with the image sensors (460) may be configured such that the optics associated with image sensor (460) of guide catheter (400, 600) provides a focal length and/or depth of field different from the focal length and/or depth of field provided by the optics associated with the image sensor of dilation catheter (200). Various suitable focal lengths and depths of field, as well as the optical elements that may provide such focal lengths and depths of field, will be apparent to those of ordinary skill in the art in view of the teachings herein.

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A guide assembly, comprising:
   (a) an elongate shaft, the elongate shaft comprising:
      (i) a proximal portion, wherein the proximal portion is rigid,
      (ii) a distal portion, wherein the distal portion is curved or bendable, wherein the distal portion is configured to fit in a nasal cavity, wherein the distal portion includes a removed portion configured to provide bendability to the elongate shaft, and
      (iii) a lumen extending from the proximal portion to the distal portion;
   (b) a core member received within the lumen of the elongate shaft, wherein the core member defines a plurality of lumens extending longitudinally, wherein a working lumen of the plurality of the lumens is configured to slidably receive a working instrument, wherein the core member is coupled with the elongate shaft, wherein the removed portion is only through the elongate shaft such that the core member remains fully intact;
   (c) a grasping feature positioned at the proximal portion of the elongate shaft; and
   (d) an imaging assembly integrated with the distal portion of the elongate shaft, wherein the imaging assembly comprises:
      (i) an image sensor, and
      (ii) a light feature configured to provide illumination.

2. The guide assembly of claim 1, wherein the removed portion includes a spiral cut, wherein the elongate shaft comprises a hypotube, wherein the spiral cut is configured to provide bendability to the hypotube.

3. The guide assembly of claim 2, wherein the spiral cut comprises a cut formed transversely through the hypotube extending in a spiral pattern longitudinally through the length of the distal portion, wherein the core member is a polymeric inner core, and wherein the spiral cut is only through the hypotube such that the polymeric inner core remains fully intact.

4. The guide assembly of claim 1, wherein the plurality of lumens of the core member comprise the working lumen and at least two access lumens, and wherein the access lumens are configured to receive one or more wires or illumination fibers to connect to the image sensor.

5. The guide assembly of claim 4, wherein the image sensor is positioned adjacent to the working lumen.

6. The guide assembly of claim 4, wherein the image sensor connects to a wire bundle that is threaded through one or more of the access lumens and out of a proximal opening of the proximal portion.

7. The guide assembly of claim 1, wherein the distal portion comprises a flexible portion and a blunt distal tip, and wherein the blunt distal tip comprises the light feature that includes a plurality of distinct light sources.

8. The guide assembly of claim 7, wherein the plurality of distinct light sources is configured to project light distally from the blunt distal tip to illuminate a visualization area that is disposed distally of the blunt distal tip, wherein the light feature includes two lenses disposed within the blunt distal tip connected to two corresponding illumination fibers.

9. The guide assembly of claim 1, wherein the imaging assembly further comprises one or more lens elements or one or more optically transmissive features that are positioned distal to the image sensor and are configured to enhance imaging through the image sensor.

10. A guide assembly, comprising:
(a) an elongate shaft configured to cooperate with a working device, the elongate shaft comprising:
    (i) a proximal region, wherein the proximal region is rigid, and
    (ii) a distal region, wherein the distal region includes a bent portion, wherein the bent portion includes an optically transmissive window, wherein the optically transmissive window is proximal to a distal most end of the distal region, wherein the optically transmissive window extends completely around the entire circumference of the elongate shaft;
(b) a grasping feature positioned at the proximal region of the elongate shaft; and
(c) an illuminating feature, wherein the illuminating feature is configured to provide light to the optically transmissive window of the elongate shaft.

11. The guide assembly of claim 10, wherein the illuminating feature comprises:
    (i) at least one light source located in the grasping feature, and
    (ii) at least one optical fiber or light pipe extending from the light source to the optically transmissive window.

12. The guide assembly of claim 10, wherein the optically transmissive window comprises a transparent light conducting polymer.

13. The guide assembly of claim 10, wherein the illuminating feature comprises an illuminating array that includes a plurality of light emitters disposed circumferentially around the illuminating array, wherein the light emitters are configured to provide the light to the optically transmissive window of the elongate shaft.

14. The guide assembly of claim 10, wherein the elongate shaft further comprises an exterior tube and an interior light communicating portion, wherein the interior light communicating portion is in communication with the illuminating feature and is configured to transfer the light from the illuminating feature through the elongate shaft to the optically transmissive window.

15. The guide assembly of claim 10, wherein the elongate shaft further comprises a plurality of optical fibers extending from the illuminating feature to the optically transmissive window, such that the optical fibers convey the light along the length of the elongate shaft instead of having an interior light communicating portion convey the light.

16. A dilation catheter system, comprising:
(a) a guide member configured to cooperate with a working device, the guide member comprising:
    (i) a proximal region, wherein the proximal region is rigid, wherein the proximal region includes a grasping feature, and
    (ii) a distal region, wherein the distal region includes a distal end and a rigid bend proximal to the distal end, wherein the rigid bend includes an optically transmissive window that extends along a portion of the rigid bend;
(b) a dilation catheter movable relative to the guide member, wherein the dilation catheter includes an expandable dilator sized to fit within a passageway associated with a paranasal sinus; and
(c) an illuminating feature configured to provide light to the optically transmissive window such that the light is emitted from the rigid bend proximal to the distal end of the guide member.

17. The dilation catheter system of claim 16, wherein the illuminating feature comprises:
    (i) at least one light source located in the grasping feature, and
    (ii) at least one optical fiber or light pipe extending from the light source to the optically transmissive window.

18. The dilation catheter system of claim 16, wherein the guide member further comprises an exterior tube and an interior light communicating portion, wherein the interior light communicating portion is in communication with the illuminating feature and is configured to transfer the light from the illuminating feature through the guide member to the optically transmissive window, wherein the interior light communicating portion and the optically transmissive window comprise a single unitary part.

19. The dilation catheter system of claim 16, wherein the dilation catheter includes depth indication marks on an exterior surface of the dilation catheter.

20. The dilation catheter system of claim 19, wherein the depth indication marks are viewable through the optically transmissive window thereby providing enhanced visual feedback indicating the depth of advancement of the dilation catheter relative to the guide member.

\* \* \* \* \*